United States Patent [19]

Marmo et al.

[11] 4,259,355

[45] * Mar. 31, 1981

[54] CHEWING GUM CONTAINING FLAVOR COMPOSITION AND FLAVOR COMPOSITION THEREFOR

[75] Inventors: Don Marmo, Farmingdale; Frank L. Rocco, Richmond Hill, both of N.Y.

[73] Assignee: International Flavors & Fragrances Inc., New York, N.Y.

[*] Notice: The portion of the term of this patent subsequent to Jan. 4, 1994, has been disclaimed.

[21] Appl. No.: 63,593

[22] Filed: Aug. 3, 1979

Related U.S. Application Data

[63] Continuation-in-part of Ser. No. 17,580, Mar. 5, 1979, abandoned.

[51] Int. Cl.³ .............................................. A23G 3/30
[52] U.S. Cl. ................................... 426/5; 426/96; 426/651; 131/17 R; 424/49; 424/362
[58] Field of Search ........................................... 426/3-6, 426/651, 573, 96, 103, 575, 650, 98; 424/49, 362; 131/17 R

[56] References Cited

U.S. PATENT DOCUMENTS

| | | | |
|---|---|---|---|
| 2,886,440 | 5/1959 | Kramer et al. | 426/5 |
| 2,886,445 | 5/1959 | Rosenthal et al. | 426/5 |
| 2,886,446 | 5/1959 | Kramer et al. | 426/5 |
| 2,886,449 | 5/1959 | Rosenthal et al. | 426/5 |
| 3,278,521 | 10/1966 | Klug | 260/231 |
| 3,795,744 | 3/1974 | Ogawa et al. | 426/3 |
| 3,818,107 | 6/1974 | Yolles | 426/3 |
| 3,857,964 | 12/1974 | Yolles | 426/3 |
| 3,862,847 | 7/1974 | Ogawa et al. | 426/3 |
| 3,930,026 | 12/1975 | Clark | 426/3 |
| 3,962,463 | 6/1976 | Witzel | 426/5 |
| 4,001,438 | 1/1977 | Marmo et al. | 426/3 |

FOREIGN PATENT DOCUMENTS

| | | | |
|---|---|---|---|
| 2826042 | 1/1979 | Fed. Rep. of Germany | 426/3 |
| 1318799 | of 0000 | United Kingdom | 426/3 |

OTHER PUBLICATIONS

Klug, Hydroxypropyl Cellulose, A new Water Soluble Polymer, vol. 24, 51, Food Tech., Jan. 1970.
Hercules Klucel©, Hydroxypropyl Cellulose/Chem. and Phy. Properties, Hercules Inc., 1976.

*Primary Examiner*—Jeanette M. Hunter
*Attorney, Agent, or Firm*—Arthur L. Liberman

[57] ABSTRACT

Orally utilizable compositions which may be either chewing gum compositions, chewable medicinal tablets, chewing tobacco or toothpaste having an oral intake, a high flavor intensity release substantially evenly and uniformly, over an extended oral utilization time in the mouth cavity; the orally utilizable compositions containing a non-confined flavor oil, a flavor oil which is physically entrapped in solid particles and a suspending agent which is hydroxypropyl cellulose as specifically defined in U.S. Pat. No. 3,278,521, issued on Oct. 11, 1966; the non-confined flavor oil, the entrapped flavor oil and the suspension agent being premixed prior to addition to either of the chewing gum base, the chewing tobacco or the chewable medicinal tablet base, or to the toothpaste base.

6 Claims, 2 Drawing Figures

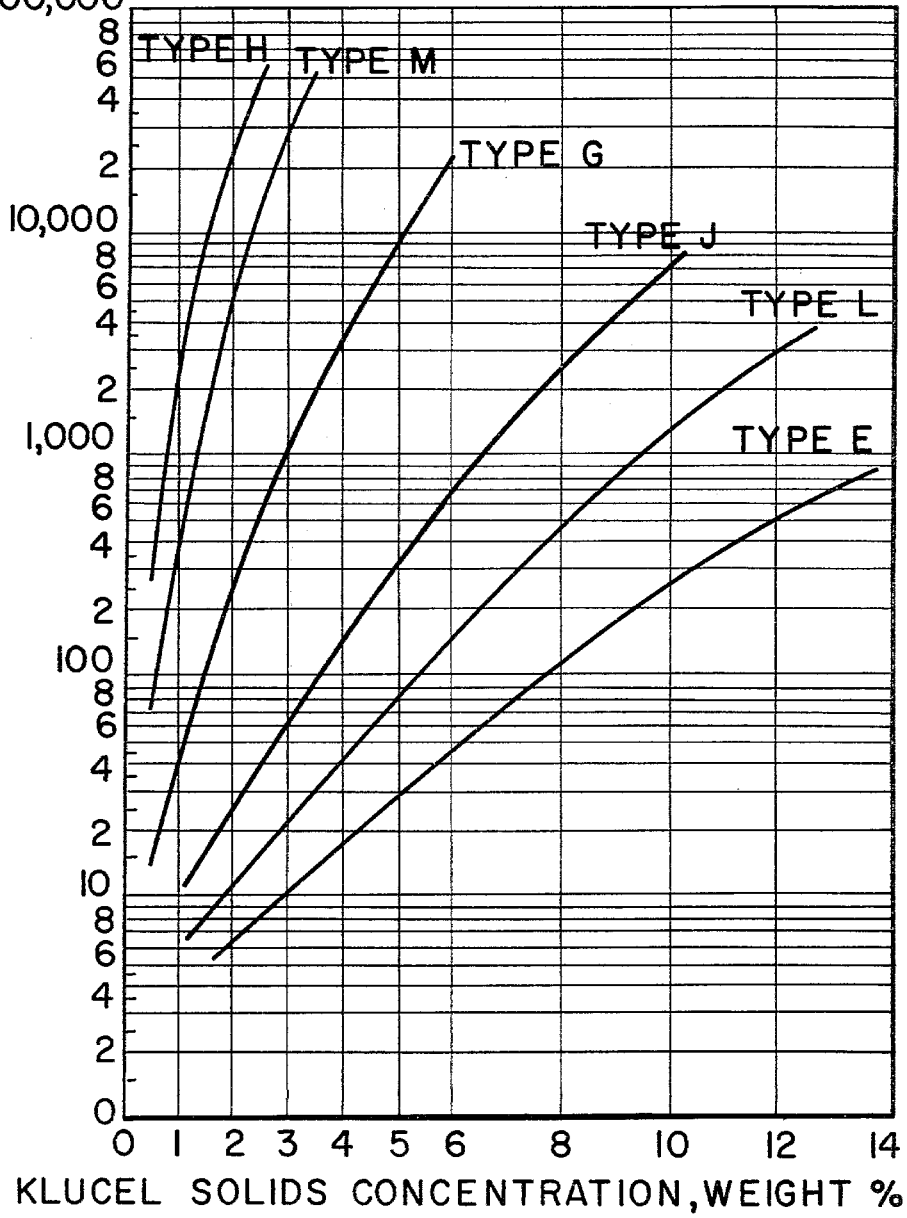

CHEWING GUM CONTAINING FLAVOR COMPOSITION AND FLAVOR COMPOSITION THEREFOR

This application is a continuation-in-part of application for U.S. Pat. Ser. No. 17,580, filed on Mar. 5, 1979 now abandoned.

BACKGROUND OF THE INVENTION

This invention relates to improved orally utilizable compositions having a flavor with good initial strength and which flavor is controllably released (under the hydrolytic conditions of the human mouth cavity) at a consistently high level over an extended period of time; to processes for preparing such orally utilizable compositions; to flavor compositions useful in preparing same and to processes for preparing such specially useful flavoring compositions.

The term "orally utilizable compositions" includes such materials as chewing gum, chewable medicinal tablets such as chewable vitamin tablets, chewing tobacco and toothpaste.

There has been considerable work performed relating to orally utilizable substances such as chewing gum, chewable medicinal tablets, chewing tobacco and toothpaste whereby such orally utilizable substances have a flavor impact both initially and over an extended period of time. Problems have arisen in attempting to create such orally utilizable compositions wherein part of the flavor is available for immediate results whereas another part provides the effect of such flavor gradually over extended periods of time. Such problems include the continuous distribution of "initial impact" and "extended release" flavor over the entire mass of the orally utilizable composition as well as commercial manufacture of same.

U.S. Pat. No. 1,526,039, for example, teaches that if an essential oil or flavoring is combined with chewing gum base in a finely divided condition, and the particles of the flavoring or oil are encased in a suitable covering so as not to contact directly the gum during manufacture, the deleterious effect of the flavoring on the gum is prevented or largely reduced. It is further stated therein that:

"When the emulsion is added to the gum base, it is thoroughly mixed therewith by the usual means employed for mixing the flavoring material with such base.

The production of the emulsion serves to break up the essential oil into fine particles and to encase these particles in the emulsifying material, so that when the emulsion is added to the gum mass, the essential oil to a large degree is prevented from coming into direct contact with the base, and from having deleterious action thereon."

U.S. Pat. No. 2,886,440 teaches a method of preparing a chewing gum characterized by "extended flavor perception time, true flavor character, and high degree of flavor release comprising the steps of forming a spray-dried emulsion of a volatile, water-immiscible flavoring agent encapsulated within finely divided particles of gelatin, and substantially uniformly distributing said gelatin encapsulated flavoring agent within an all-enveloping mass of a chewable gum base." The use of separate "fixed" and "unfixed" flavor portions is also taught but there is no disclosure therein of the principal of this invention, to wit: mixing the fixed and unfixed flavor portions with a suspension agent prior to adding to the chewing gum base.

U.S. Pat. No. 2,886,446 teaches a chewing gum comprising (i) smaller particles of gelatin characterized by faster liberation of flavor and (ii) larger particles of gelatin characterized by slower liberation of flavor, each of the gelatin particles containing dispersed therewithin, in dried emulsion form, discrete micro-droplets of a volatile water-immiscible flavoring agent, and an all-enveloping mass of a chewable gum base within which the particles are substantially uniformly distributed whereby the flavor is released substantially evenly and uniformly over the extended chewing time.

U.S. Pat. No. 2,886,445 teaches that:

"It is possible to obtain a flavoring composition, particularly adapted for use in chewing gum which permits attainment of a product characterized by extended flavor preception time, true flavor character, and release of a large proportion of flavoring agent. This flavoring composition comprises finely divided particles of a dried hardened gelatin emulsion containing discrete micro-droplets of a volatile, water-immiscible flavoring agent. Preparation of the flavoring composition of this invention may be effected by encapsulating discrete micro-droplets of volatile, water-immiscible flavoring agent within finely divided particles of a dried emulsion of hardened gelatin."

U.S. Pat. No. 2,886,449 teaches:

"A chewing gum containing a flavoring composition characterized by an extended flavor perception time, true flavor character, controlled release of a large portion of flavoring agent, and reduction in amount of flavor oil required (which) may be prepared by the process comprising forming a gelatin-coacervated flavor, and substantially uniformly distributing said gelatin-coacervated flavor within an all-enveloping mass of a chewable gum base. The product chewing gum . . . comprises . . . finely divided particles of coacervated gelatin containing a water-immiscible flavoring agent therewithin and an all-enveloping mass of a chewing gum base within which the particles are substantially distributed."

The utilization of sustained released flavor containing capsules in such materials as chewing gum and mecidinal tablets is also taught in British Pat. No. 1,205,764.

The use of sustained release flavor capsules in conjunction with polyethylene glycols (which are taught to be employed to disolventize the capsules) is set forth in British Pat. No. 1,318,799.

Furthermore, described in U.S. Pat. No. 3,920,849 may be either chewing gum compositions, chewable medicinal tablets, chewing tobacco or toothpaste having an oral intake, a high flavor intensity release substantially evenly and uniformly, over an extended oral utilization time in the mouth cavity; the orally utilizable compositions containing a non-confined flavor oil, a flavor oil which is physically entrapped in solid particles and a suspending agent such as silica, xanthan gum and ethyl cellulose; the non-confined flavor oil, the entrapped oil and the suspension agent being premixed prior to addition to either of the chewing gum base, the chewing tobacco or the chewable medicinal tablet base or the toothpaste base.

Nothing in the prior art, however, indicates the use of hydroxypropyl cellulose as defined in U.S. Pat. No. 3,278,521 issued on Oct. 11, 1966 for taking the place of the suspension agents of U.S. Pat. No. 3,920,849.

Furthermore, German Offenlengungsschrift No. 2,826,042 published on Jan. 4, 1979 relying on Austrian priority document A4305-77 of June 17, 1977 discloses a condiment consisting of a salt admixed with (a) from 0.1 up to 0.5 weight percent of a terpene-free lemon oil bonded to a powdery character and (b) a terpene-free liquid lemon oil. In German Offenlengungsschrift No. 2,826,042 the condiment is prepared by mixing the dry salts with component (a), spraying the mixture with (b) and mixing through a mixer such as a mixing screw. Nothing in Offenlengungsschrift No. 2,826,042 implies that a hydroxypropyl cellulose material can be used as a suspending agent for the terpene-free liquid lemon oil.

The hydroxypropyl cellulose derivatives useful in the practice of our invention are particularly described in a paper entitled "Functional Helpmate To Development . . . Hydroxypropyl Cellulose/A New Water Soluble Cellulose Polymer", Klug, Vol. 24, 51, Food Technology, January, 1970 and a pamphlet entitled "Klucel ®-/Hydroxypropyl Cellulose/Chemical and Physical Properties Published by Hercules Incorporated, 1976".

BRIEF DESCRIPTION OF THE DRAWING

FIG. 2: sets forth a graph of solids concentration (weight percent) of hydroxypropyl cellulose, Klucel$^R$ brand (manufactured by Hercules Corporation of Wilmington, Delaware) versus Brookfield viscosity at 25° C., centipoises; for types E, L, J, G, M and H forms of KLUCEL$^R$ brand of hydroxypropyl cellulose.

THE INVENTION

Figure 1:
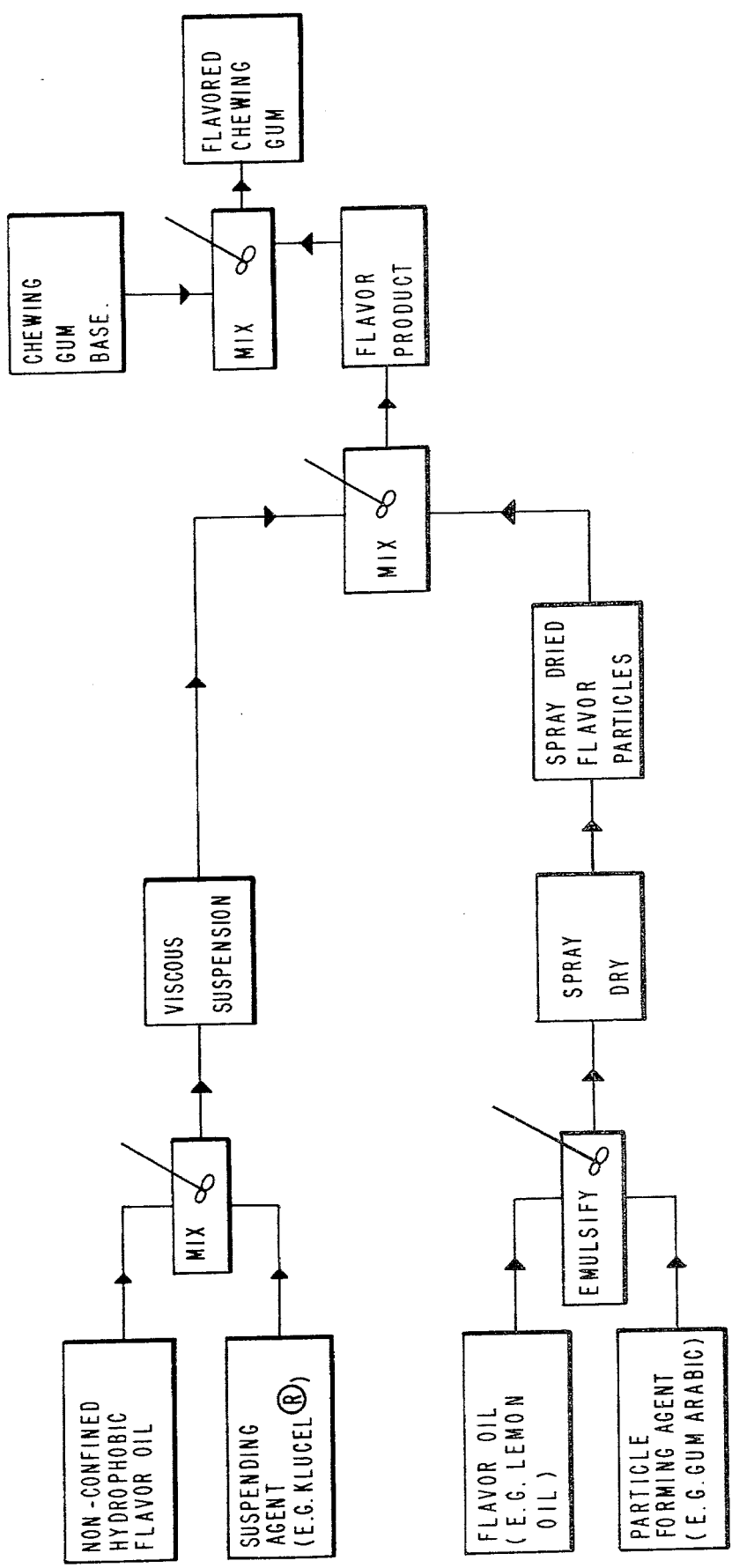
FIG. 1: sets forth a block diagram flow sheet indicating the preparation of the flavored beverage powder as well as the flavored chewing gum of our invention as more fully described in Examples A-W and I-XCII, infra.

This invention relates to improved orally utilizable compositions such as chewing gum, chewable medicinal tablets, chewing tobacco and toothpaste having a flavor with good evenly distributed initial strength and which flavor is controllably released with continuous non-interrupted high flavor impact over an extended period of time; to processes for preparing the same; to flavor compositions useful in preparing same and to processes for preparing such flavoring compositions.

Chewing gum and chewable medicinal tablets may comprise a substantially water insoluble, chewable, plastic gum base such as chicle, or substitutes therefor, including jelutong, guttakay, rubber or certain comestible natural or synthetic resins or waxes. Incorporated with the gum base, and in intimate admixture therewith, may be plasticizers or softening agents, e.g., glycerine; flavoring agents, e.g., oil of wintergreen, oil of spearmint, oil of peppermint, licorice, fruit flavors, spice oils, etc.; or sweetening agents which may be sugars including sucrose or dextrose and/or they may be artificial sweeteners such as cyclamates or saccharin. Other optional ingredients may also be present.

Chewing tobacco may comprise specially grown tobacco for chewing which would include 85 percent Pennsylbania Leaf Tobacco having a "casing" spray dried at a rate of about 25 percent up to about 40 percent which casing would contain such ingredients as corn syrup, licorice, glycerin, fig juice, prune juice and as is the case in this invention, a flavor material. The resultant product is redried to a moisture content of between 10 and 30 percent.

Toothpastes may comprise four groups of additives:

Group A: Glycerine; distilled water; sodium benzoate; if desired, artificial sweetener such as sodium saccharin and, if desired, stannous fluoride.

Group B: A basic pH buffer as calcium carbonate and/or dicalcium phosphate.

Group C: A foaming agent such as sodium n-lauroyl sacrosinate.

Group D: A flavor material.

A standard technique for formulating the above groups into the toothpaste is exemplified as follows:

1. The ingredients in Group A are stirred and heated in a steam jacketed kettle to 160° F.
2. Stirring is continued for an additional three to five minutes to form a homogeneous gel.
3. The powders of Group B are added to the gel, while mixing until a homogeneous paste is formed.
4. With stirring, the flavor of D is added and lastly the foaming agent.
5. The resultant slurry is then blended for 1 hour. The completed paste is then transferred to a three roller mill and then homogenized, and finally tubed.

It is found that when most flavored chewing gums such as slab gums, and when most flavored chewing tobacco and chewable medicinal tablets are chewed and when most toothpastes are used in a normal toothbrushing procedure of 1–2 minutes, the initial perception of flavor appears after a minute or more at a low level, and after 3 or 4 minutes of chewing the flavor intensity drops to an uninteresting level. It is also found upon analysis in several instances that chewable medicinal tablets or chewing gum or tobacco chewed or toothpaste utilized for as long as thirty minutes may retain as much as 60 percent of the flavor initially present, and that this part of the flavoring agent is thus not effectively used.

It is an object of this invention to provide an orally utilizable composition containing a flavoring composition characterized by (i) an almost instantaneous flavor perception and (ii) over an extended period of time controlled constant and continuous, non-interrupted high impact flavor release.

A second object of this invention is to increase the total amount of flavor released during the chewing period of chewing gums, chewing tobacco and chewable medicinal tablets or during the toothbrushing period of toothpastes containing the herein described flavoring composition.

Other objects of this invention will be apparent to those skilled in the art from the following detailed description of the invention.

It has now been discovered that it is possible to obtain an orally utilizable composition, such as chewing gum, chewable medicinal tablets, chewing tobacco and toothpaste containing a flavoring composition which provides almost instantaneous flavor release, extended high intensity constant flavor perception time, true flavor character and controlled release of the major proportion of flavoring agent initially present in the flavoring composition. This flavoring composition of our invention consists essentially of:

a. From about 3 up to about 7 parts by weight of a non-confined hydrophobic flavor oil;

b. From about 3 up to about 7 parts by weight of a hydrolytically releaseable flavor oil physically entrapped in an edible solid material, said solid material having a particle size of from about 5 microns up to about 400 microns said physically entrapped flavor oil being organoleptically compatible with said non-confined hydrophobic flavor oil; and c. From about 0.1 up to about 1 part by weight of a solid suspending agent which is a hydroxypropyl cellulose having a molecular weight of from about 50,000 up to 800,000 and a viscosity in solution as defined according to FIG. 2. Preparation of the flavoring composition employed in the orally utilizable compositions, of our invention may be effected by:

1. Admixing
   a. From about 3 up to about 7 parts by weight of a non-confined hydrophobic flavor oil; and
   b. From about 0.1 up to about 1 part by weight of a solid suspending agent which is a hydroxypropyl cellulose having a molecular weight of from 50,000 up to 800,000 and a viscosity defined according to the graph in FIG. 2; thereby forming a first suspension; and then
2. Admixing said first suspension with from about 3 up to about 7 parts by weight of a hydrolytically releasable flavor oil physically entrapped in an edible solid material, said solid material having a particle size of from about 5 microns up to about 400 microns thereby forming a second suspension, said physically entrapped flavor oil being organoleptically compatible with said non-confined hydrophobic flavor oil. The orally utilizable composition or our invention such as chewing gum, chewable medicinal tablets, chewing tobacco, and toothpaste may be prepared by the steps of:
   1. Admixing
      a. From about 3 up to about 7 parts by weight of a non-confined hydrophobic flavor oil; and
      b. From about 0.1 up to about 1 part by weight of a solid suspending agent which is a hydroxypropyl cellulose having a molecular weight of from 50,000 up to 800,000 and a viscosity defined according to FIG. 2 thereby forming a first suspension (if desired an additional product stabilizer such as propylene glycol may also be incorporated into the mixture);
   2. Admixing said first suspension with from about 3 up to about 7 parts by weight of a hydrolytically releasable flavor oil physically entrapped in an edible solid material, said solid material having a particle size of from about 5 microns up to about 400 microns (preferably from 70 up to 300 microns) thereby forming a second suspension, said physically entrapped flavor oil being organoleptically compatible with said non-confined hydrophobic flavor oil; and
   3. Substantially uniformly distributing said second suspension with an all-enveloping base selected from the group consisting of (1) chewing gum base, (2) chewable vitamin tablet base, (3) chewing tobacco, and (4) toothpaste base, depending upon the ultimately desired orally usable composition.

The solid physical entrapment material used to entrap the hydrolytically releasable flavor oil may be of various convenient physical shapes, e.g., capsules having gelatin shells; particles of dextrin and/or modified food starch and/or gum acacia capable of adsorbing and/or adsorbing and retaining flavor oils until exposed to the hydrolytic conditions of the human mouth.

The gelatin which may be employed in this invention may be any of the grades and types of gelatin, including those obtained from e.g., tanner's stock, ossein, pigskin, etc. The Bloom of the gelatin which is employed may vary widely, although a particularly rapid release from that portion of the flavor which is physically entrapped may be obtained by use of gelatin having a Bloom of about 50 or less, the Bloom may be as high as 200 or even higher. Although the pH of the gelatin solution employed may fall within the range of 2 to 10, it is preferred that it be maintained in the acid region, e.g., 2 to 5.

In carrying out the process of our invention, sustained release flavors are prepared by combining non-confined flavor oils with encapsulated or physically entrapped flavor oils. These combinations are fashioned so that the free oil is bound in a network of physically entrapped flavor and suspending agent. The thixotropic pastes, or free flowing powders which result are products where the unconfined flavor oil, the "encapsulated" or physically entrapped flavor oil and suspending agent are held together by physical forces.

When acacia is used as the entrapment agent for the physically entrapped flavor oil, a suitable product results when, for example, the following combination is prepared:

| Ingredient | Parts by Weight |
|---|---|
| Oil Peppermint | 48.4 |
| Physically entrapped peppermint oil | 48.4 |
| KLUCEL ® type HF manufactured by Hercules Incorporated of Wilmington, Delaware having a molecular weight of approximately 800,000 | 3.2 |

Acacia may be replaced with various modified food starches, such as Capsul ® manufactured by the National Starch and Chemical Company of New York, New York, or dextrins such as Schardinger Dextrins produced according to Example 1 to 14 of U.S. Pat. No. 3,472,835 issued on Oct. 14, 1969; or such dextrins as "Nadex" ® manufactured by the National Starch and Chemical Company of New York, New York. The physical forces of these modified starches or dextrins are different from those of acacia, so that when such formulations as the above formulation are prepared using a modified starch or dextrin (entrapped flavor oil a thin rapidly separating unstable mixture results. This difficulty is corrected, however, by making adjustment in the formulation by adding low molecular weight polyhydroxy alkanes such as propylene glycol to modify the physical forces of the system.

The following composition, for example, where modified starch is used as the physically entrapment material forms a stable product:

| Ingredient | Parts by Weight |
|---|---|
| Oil of Peppermint | 47.25 |
| Physically entrapped Peppermint oil produced by the spray-drying of an emulsion of modified starch, peppermint oil and water | 47.25 |
| KLUCEL ® HF | 5.00 |
| Propylene Glycol | 0.50 |

The Propylene Glycol adjusts the forces and bonding network improving the product stability.

The preparation of sustained release flavors of the various types requires formulations produced in accordance with the physical properties of the specific flavor oil and encapsulating agent desired.

In the case of preparing dry, free flowing sustained release flavors, compositions having a high ratio (from 2.3:1 up to 5:1) of physically entrapped oil:non-confined oil are used, for example:

| Ingredient | Parts by Weight |
| --- | --- |
| (a) Peppermint Flavor | |
| Non-confined oil of peppermint | 20 |
| KLUCEL ® MF having a molecular weight of 700,000 | 9 |
| Physically entrapped peppermint oil produced by spray drying an emulsion of gum acacia, peppermint oil and water. | 71 |
| (b) Cherry Flavor | |
| Non-confined cherry flavor | 26 |
| KLUCEL ® MF | 9 |
| Physically entrapped cherry flavor produced by spray-drying an emulstion of modified food starch, cherry flavor and water. | 65 |

These flavors have an appearance identical to standard, commercial spray dried flavors but have much more aroma resulting from the presence of the non-confined flavor oil portion which is mixed with the physically entrapped, e.g., spray dried, or encapsulated portion.

The value of using these sustained release flavors, in orally utilizable compositions such as chewing gum and chewing tobacco, other than the fact that they provide ease and convenience when used in flavoring products, as compared to adding a free flavor oil portion and an encapsulated flavor oil portion separately is:

A. The non-confined flavor oil is not "free" in the flavor composition of our invention release form; but it is bonded by physical forces in a network with the physically entrapped or "encapsulated" oil and suspension agent, and is therefore highly protected from its environment compared to the case of a non-confined flavor oil by itself; and B. A more uniform distribution of flavor exists as compared with a product created by means of the separate addition of (i) liquid non-confined and (ii) dry physically entrapped flavor components.

In the case of powdered flavor mixes which contain physically entrapped, e.g., encapsulated flavors that are reconstituted before use, sustained release flavors are also of value. Encapsulated flavors have very little aroma; only that aroma evolved from the residual oil which is not enrobed. A jar of cherry flavored drink powder while having the proper amount of flavor when reconstituted, from its "encapsulated" flavor, lacks suitable "jar aroma" when opened by the consumer. The use of the dry sustained release cherry flavor of our invention provides the drink mix with good jar aroma as well as the proper flavor when reconstituted.

In carrying out one particular aspect of the process of this invention, a solution of physical entrpment agent, e.g., gelatin, modified food starch, dextrin, or gum acacia, may be formed containing 5 to 100 parts of entrapment agent per one hundred parts of water, the latter being preferably at a temperature of 90° F. to 180° F. during dissolution of the entrapment agent.

The solution is allowed to cool preferably to 33° F. to 75° F., and it is then solidified by spray-drying.

Prior to the spray-drying of the solution of entrapment agent and preferably after cooling to 80° F. to 140° F., the desired volatile, water-immiscible flavoring agent may be added to the solution and homogenized to form an emulsion. The flavoring agents which may be employed include oil of peppermint, cherry flavor, orange oil, lemon flavor, lime flavor, oil of spearmint, fruit essences, licorice, spice oils and the like. The selected flavoring agent may be added in an amount equal to 10 to 100 percent of the weight of the entrapment agent. Examples of the physically entrapped flavor material utilizable in our invention are:

a. Cherry flavor oil physically entrapped in dextrin;
b. Cherry flavor oil encapsulated in gelatin capsules;
c. Cherry flavor oil entrapped in gum acacia;
d. Lemon flavor oil physically entrapped in dextrin;
e. Lemon flavor oil encapsulated in gelatin capsules;
f. Lemon flavor oil entrapped in gum acacia;
g. Lime flavor oil physically entrapped in dextrin;
h. Lime flavor oil encapsulated in gelatin capsules;
i. Lime flavor oil entrapped in gum acacia;
j. Peppermint flavor oil physically entrapped in dextrin;
k. Peppermint flavor oil encapsulated in gelatin capsules;
l. Peppermint flavor oil entrapped in gum acacia;
m. Oil of wintergreen physically entrapped in dextrin;
n. Oil of wintergreen encapsulated in gelatin capsules;
o. Oil of wintergreen entrapped in gum acacia;
p. Orange flavor oil physically entrapped in dextrin;
q. Orange flavor oil encapsulated in gelatin capsules;
r. Orange flavor oil entrapped in gum acacia;
s. Cherry flavor oil entrapped in modified food starch;
t. Lemon flavor oil entrapped in modified food starch;
u. Lemon flavor oil entrapped in modified food starch;
v. Peppermint flavor oil entrapped in modified food starch;
w. Oil of wintergreen entrapped in modified food starch; and
x. Orange flavor oil entrapped in modified food starch.

When the emulsion of flavoring agent in solution of entrapment agent is solidified as by spray-drying the resultant spray-dried emulsion may have the flavoring agent in the form of discrete micro-droplets encapsulated in very fine particles of dried gelatin or it may have the flavor oil absorbed into solid particles as in the case with gum arabic or gum acacia. The solid spray-dried emulsion will be in powder form which may be 5 microns to 400 microns. The preferred size being 70–300 microns.

Formation of a flavored chewing gum, for example, may be effected by:

1. Admixing
   a. From about 3 up to about 7 parts by weight of a non-confined hydrophobic flavor oil; and
   b. from about 0.1 up to about 1 part by weight of a solid suspending agent which is hydroxypropyl cellulose having a molecular weight of from about 50,000 up to about 800,000 and having a viscosity defined according to FIG. 2; thereby forming a first suspension;

2. Admixing said first suspension with from about 3 up to about 7 parts by weight of a hydrolytically releasable flavor oil physically entrapped in an edible solid material, said solid material having a particle size of from about 5 microns up to about 400 microns thereby forming a second suspension said physically entrapped flavor oil being organoleptically compatible with said nonconfined hydrophobic flavor oil; and 3. Substantially uniformly distributing said second suspension within an all-enveloping mass of a chewable gum base.

A preferred composition has 0.5–3.0 percent of flavoring composition in 97–99.5 percent by weight of gum base, more preferably, 1 percent flavoring composition: 99 percent gum base. Typically the gum base will be chicle, although it may be jelutong, guttakay, etc. Other ingredients including sweetening agents, coloring agents, etc. may be present in desired amount.

Although the orally utilizable compositions of this invention be prepared from a single flavoring agent, e.g., cherry flavor, it is possible to extend the range of properties of the gum by use of combinations of two or more spray-dried flavoring compositions and two or more non-confined flavors which may or may not be different but which are organoleptically compatible with the physically entrapped flavors. For example, it is possible to separately prepare spray-dried flavoring compositions from gelatins of various Blooms, and then to add these compositions to the first suspension of flavor oil and suspension agent and also add the spray-dried flavor to the such material as chewing gum, separately. Thus such a chewing gum may, for example, contain a mixture of flavoring compositions prepared from a low Bloom gelatin, (characterized by a rapid flavor release) and a high Bloom gelatin (characterized by a longer flavor release) as well as non-confined flavor oil (very rapid release). The properties of the chewing gum product will be intermediate to the properties obtained from each of the flavoring compositions when used separately. Specifically, if a flavoring composition formed from 50 Bloom gelatin is mixed with a flavoring composition formed from 200 Bloom gelatin, and the mixture is both (i) added to a flavor oil and suspension agent which composition is added to chewing gum and (ii) added to a chewing gum alone, the product may have a flavor release which is substantially more even over the chewing gum period than is the case when a single flavoring composition just containing the entrapped and non-confined flavor oil and suspension agent is employed.

Similarly, it is possible to modify the properties of the product gum by use of mixtures of spray-dried flavoring compositions characterized by different ratios of entrapment agent to flavor oil. If, for example, a composition containing 10 percent flavoring agent and 90 percent gelatin is mixed with one containing 50 percent flavoring agent and 50 percent gelatin the resulting blended flavoring composition, after adding non-confined flavor oil and suspension agent, will yield a chewing gum having a more even (relating to duration of chewing time) liberation of flavor than is obtained by use of either flavoring agent alone.

Liberation of flavor of the orally utilizable composition of this invention may also be modified in a controlled manner to obtain an even, sustained flavor level from the time that use (e.g., chewing) in the mouth begins and thereafter for a protracted period of time far in excess of that obtained today in any such chewing gum, chewing tobacco, chewable medicinal tablet or toothpaste, by using various mixtures of flavoring compositions (a) having different particle size of physically entrapped flavor, (the resulting product deriving much of its initial flavor from the smaller particles and much of its later flavor from the larger particles); or (b) formed from gelatins of different pH, (the composition formed from gelatin of higher pH (e.g., 6) giving quick release of flavor, while that formed from lower pH (e.g., 2.5) giving slower release).

A particularly desirable flavor composition of our invention contains unfixed flavor, spray-dried flavor, and suspension agent in proportions of about 1:1:0.1. This product is characterized by an interesting or pleasing flavor level which may start at 0.25 seconds and last for 27–28 minutes. Over substantially its entire period of flavor release, the flavor level is higher than that of the standard gum, and the flavor is continuous, rich, full, and true.

It is particularly characteristic of the orally utilizable compositions of this invention, that they have almost instantaneous to very early flavor perception when used in the mouth. Usually flavor is apparent in not more than 0.25 seconds when orally utilizable compositions are prepared in accordance with this invention. Prior art chewing gums containing only free unfixed flavor have initial flavor perception after 4–5 seconds and frequently after times as long as one minute.

It is also characteristic of our orally utilizable compositions that they retain the flavors under conditions of vigorous mouth use for extended periods which may be triple that of compositions heretofore known to those skilled in the art. For example, the flavor perception time may be as long as twenty minutes, in contrast, to the usual 3–10 minutes which is the flavor perception timne of comparable products heretofore known (e.g., U.S. Pat. No. 2,886,440).

The greater availability of flavor by use of the flavoring compositions herein described also permits attainment of high flavor level in the orally utilizable composition with use of lower amounts of the flavoring oils.

Orally utilizable compositions prepared with the flavor composition in accordance with this invention, have a flavor character more nearly that of the original flavor oil than chewing gum prepared by merely the direct incorporation of the flavoring oil into the chewing gum without concomitant use of the physically entrapped flavors and suspension agents.

The term "encapsulate" may be used to describe the relation of the entrapment agent and the flavoring agent and means that the latter, in the form of a spray-dried emulsion of discrete micro-droplets, droplets, is distributed substantially uniformly within or in the interstices of finely divided particles of the former. The flavoring agent is locked in within the entrapment agent (e.g., gelatin, gum acacia, dextrin and modified food starch to the extent that the former is released substantially only as the molecules of entrapment agent are dissolved from the surface of the individual entrapment agent particles by the hydrolytic action of salivary liquids.

The following Examples A–W illustrate processes for preparing the individual flavor components necessary to produce the flavor composition of our invention.

EXAMPLE A

CHERRY FLAVOR FORMULATION

The following mixture is prepared:

| Ingredient | Parts by Weight |
| --- | --- |
| Eugenol | 1.75 |
| Cinnamic Aldehyde | 4.50 |
| Anisyl Acetate | 6.25 |
| Anisic Aldehyde | 9.25 |
| Ethyl Oenanthate | 12.50 |
| Benzyl Acetate | 15.50 |
| Vanillin | 25.00 |
| Ethyl Methyl Phenyl Glycidate | 25.00 |
| Ethyl Butyrate | 37.25 |
| Amyl Butyrate | 50.00 |
| Tolyl Aldehyde | 125.00 |
| Benzaldehyde | 558.00 |
| Alcohol 95% | 130.00 |

EXAMPLE B

LEMON FLAVOR FORMULATION

| Ingredient | Parts by Weight |
| --- | --- |
| Methyl Heptenone | 0.50 |
| Terpineol | 1.00 |
| Linallol | 1.00 |
| n-Decanal | 1.25 |
| n-Octanal | 1.25 |
| Geranyl Acetate | 1.75 |
| Citral | 60.00 |
| Oil of lemon, cold pressed | 100.00 |
| Orange Terpenes | 833.25 |

EXAMPLE C

LIME FLAVOR FORMULATION

The following mixture is prepared:

| Ingredient | Parts by Weight |
| --- | --- |
| Cymene | 1.0 lb. |
| Dipentene | 1.0 lb. |
| Oil of Lime Distilled | 3.0 lb. |
| 6.0 oz. av. citral Terpineol | 2.0 lb. |
| Lemon Terpenes | 10.0 lb. |
| 10 oz. av. Lime Terpenes | 82.0 lb. |

EXAMPLE D

20 Grams of the flavor composition of Example A is emulsified in a solution containing 300 gm gum acacia and 700 gm water. The emulsion is spray-dried with a Bowen Lab Model Drier utilizing 250 c.f.m. of air with an inlet temperature of 500° F., an outlet temperature of 200° F., and a wheel speed of 50,000 r.p.m.

EXAMPLE E

20 Grams of the flavor composition of Example B is emulsified in a solution containing 300 gms gum acacia and 700 gm water. The emulsion is spray-dried with a Bowen Lab Model Drier utilizing 250 c.f.m. of air with an inlet temperature of 500° F., an outlet temperature of 200° F., and a wheel speed of 50,000 r.p.m.

EXAMPLE F

20 Grams of the flavor composition of Example C is emulsified in a solution containing 300 gm gum acacia and 700 gm water. The emulsion is spray-dried with a Bowen Lab Model Drier utilizing 260 c.f.m. of air with an inlet temperature of 500° F., an outlet temperature of 200° F., and a wheel speed of 50,000 r.p.m.

EXAMPLE G

50 Grams of the flavor composition of Example A is emulsified in a solution containing 300 gm gum acacia and 700 gm water. The emulsion is spray-dried with a Bowen Lab Model Drier utilizing 250 c.f.m. of air with an inlet temperature of 500° F., an outlet temperature of 200° F., and a wheel speed of 50,000 r.p.m.

EXAMPLE H

80 Grams of the flavor composition of Example B is emulsified in a solution containing 300 gm gum acacia and 700 gm water. The emulsion is spray-dried with a Bowen Lab Model Drier utilizing 250 c.f.m. of air with an inlet temperature of 500° F., an outlet temperature of 200° F., and a wheel speed of 50,000 r.p.m.

EXAMPLE J

120 Grams of the flavor composition of Example C is emulsified in a solution containing 300 gm gum acacia and 700 gm water. The emulsion is spray-dried with a Bowen Lab Model Drier utilizing 250 c.f.m. of air with an inlet temperature of 500° F., an outlet temperature of 200° F., and a wheel of 50,000 r.p.m.

EXAMPLE K

130 Grams of oil of peppermint redistilled is emulsified in a solution containing 300 gm of "Nadex" dextrin (manufactured by National Starch and Chemical Co. of New York, N.Y.) and 700 gm of water. The emulsion is spray-dried with a Bowen Lab Model Drier utilizing 250 c.f.m. of air with an inlet temperature of 500° F., an outlet temperature of 200° F., and a wheel speed of 50,000 r.p.m.

EXAMPLE L 150 gm of oil of peppermint natural is emulsified in a solution containing 300 gm of "Capsul" modified food starch of National Starch and Chemical Co. of New York, N.Y. and 700 gm of water. The emulsion is spray-dried with a Bowen Lab Model Drier utilizing 250 c.f.m. of air with an inlet temperature of 500° F., an outlet temperature of 200° F., and a wheel speed of 50,000 r.p.m.

EXAMPLE M

10 Parts by weight of 50 Bloom pigskin gelatin is added to 90 parts by weight of water at a temperature of 150° F. The mixture is agitated until the gelatin completely dissolved and the solution is cooled to 120° F. 20 Parts by weight of methyl salicylate (oil of wintergreen) is added to the solution which is then homogenized to form an emulsion having particle size typically in the range of 2–5 microns. This material is kept at 120° F. under which conditions the gelatin will not jell.

Coacervation is induced by adding, slowly and uniformly 40 parts by weight of a 20 percent aqueous solution of sodium sulphate. During coacervation, the gelatin molecules are deposited uniformly about each oil droplet as a nucleus.

Gelatin is effected by pouring the heated coacervate mixture into 1,000 parts by weight of 7 percent aqueous solution of sodium sulphate at 65° F. The resulting jelled coacervate may be filtered and washed with water at temperature below the melting point of gelatin, to remove the salt.

Hardening of the filtered cake, in this example, is effected by washing with 200 parts by weight of 37 percent solution of formaldehyde in water. The cake is then washed to remove residual formaldehyde.

EXAMPLE N

10 Parts by weight of 50 Bloom pigskin gelatin is added to 90 parts by weight of water at a temperature of 150° F. The mixture is agitated until the gelatin completely dissolved and the solution is cooled to 120° F. 20 Parts by weight of the flavor of Example A is added to the solution which is then homogenized to form an emulsion having particle size typically in the range of 2-5 microns. This material is kept at 120° F. under which conditions the gelatin will not jell.

Coacervation is induced by adding, slowly and uniformly 40 parts by weight of a 20 percent aqueous solution of sodium sulphate. During coacervation, the gelatin molecules are deposited uniformly about each oil droplet as a nucleus.

Gelatin is effected by pouring the heated coacervate mixture into 1,000 parts by weight of 7 percent aqueous solution of sodium sulphate at 65° F. The resulting jelled coacervate may be filtered and washead with water at temperatures below the melting point of gelatin, to remove the salt.

Hardening of the filtered cake, in this example, is effected by washing with 200 parts by weight of 37 percent solution of formaldehyde in water. The cake is then washed to remove residual formaldehyde.

EXAMPLE O

10 Parts by weight of 50 Bloom pigskin gelatin is added to 90 parts by weight of water at a temperature of 150° F. The mixture is agitated until the gelatin completely dissolved and the solution is cooled to 120° F. 20 Parts by weight of the flavor of Example B is added to the solution which is then homogenized to form an emulsion, having particle size typically in the range of 2-5 microns. This material is kept at 120° F. under which conditions the gelatin will not jell.

Coacervation is induced by adding, slowly and uniformly 40 parts by weight of a 20 percent aqueous solution of sodium sulphate. During coacervation, the gelatin molecules are deposited uniformly about each oil droplet as a nucleus.

Gelatin is effected by pouring the heated coacervate mixture into 1,000 parts by weight of 7 percent aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37 percent solution of formaldehyde in water. The cake is then washed to remove residual formaldehyde.

EXAMPLE P

10 Parts by weight of 50 Bloom pigskin gelatin is added to 90 parts by weight of water at a temperature of 150° F. The mixture is agitated until the gelatin completely dissolved and the solution is cooled to 120° F. 20 Parts by weight of the flavor of Example C is added to the solution which is then homogenized to form an emulsion, having particle size typically in the range of 2-5 microns. This material is kept at 120° F. under which conditions the gelatin will not jell.

Coacervation is induced by adding, slowly and uniformly 40 parts by weight of a 20 percent aqueous solution of sodium sulphate. During coacervation, the gelatin molecules are deposited uniformly about each oil droplet as a nucleus.

Gelatin is effected by pouring the heated coacervate mixture into 1,000 parts by weight of 7 percent aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37 percent solution of formaldehyde in water. The cake is then washed to remove residual formaldehyde.

EXAMPLE Q

A 40 percent dextrin solution is freeze-dried. This is accomplished by a conventional technique such as that described in column 4 of U.S. Pat. No. 3,404,007.

The freeze-dried material is then milled to a particle size of 20-40 mesh.

100 Grams of this freeze-dried material are then combined with 50 grams of orange oil. This is accomplished by mixing the materials in a suitable blender, such as a ribbon blender. This results in a dry, free-flowing powder having the advantages heretofore described. To ensure against atmospheric reaction or vaporization of the orange oil in the solid matrix, the powder is given a protective coating to seal the entrances to the interstices or cavities in the porous particulate matrix. One suitable form of coating is a dextrin solution which has the property of forming an impermeable film for preventing the escape of permeation of the flavoring oil.

EXAMPLE R

A 40 percent dextrin solution is freeze-dried. This is accomplished by a conventional technique such as that described in column 4 of U.S. Pat. No. 3,404,007. The freeze-dried material is then milled to a particle size of 20-40 mesh.

100 Grams of this freeze-dried material are then combined with 50 grams of the flavor of Example A. This is accomplished by mixing the materials in a suitable blender, such as a ribbon blender. This results in a dry, free-flowing powder having the advantages heretofore described. To ensure against atmospheric reaction of vaporization of the flavor of Example A in the solid matrix, the powder is given a protective coating to seal the entrances to the interstices or cavities in the porous particulate matrix. One suitable form of coating is a dextrin solution which has the property of forming an impermeable film for preventing the escape of permeation of the flavoring oil.

EXAMPLE S

A 40 percent dextrin solution is freeze-dried. This is accomplished by a conventional technique such as that described in column 4 of U.S. Pat. No. 3,404,007. The freeze-dried material is then milled to a particle size of 20-40 mesh.

100 Grams of this freeze-dried material are then combined with 50 grams of the flavor of Example B. This is accomplished by mixing the materials in a suitable blender, such as a ribbon blender. This results in a dry, free-flowing powder having the advantages heretofore described. To ensure against atmospheric reaction of vaporization of the flavor of Example B in the solid matrix, the powder is given a protective coating to seal the entrances to the interstices or cavities in the porous particulate matrix. One suitable form of coating is a dextrin solution which has the property of forming an impermeable film for preventing the escape of permeation of the flavoring oil.

EXAMPLE T

A 40 percent dextrin solution if freeze-dried. This is accomplished by a conventional technique such as that described in column 4 of U.S. Pat. No. 3,404,007. The freeze-dried material is then milled to a particle size of 20–40 mesh.

100 Grams of this freeze-dried material are then combined with 50 grams of the flavor of Example C. This is accomplished by mixing the materials in a suitable blender, such as a ribbon blender. This results in a dry, free-flowing powder having the advantages heretofore described. To ensure against atmospheric reaction or vaporization of the flavor of Example C in the solid matrix, the powder is given a protective coating to seal the entrances of the interstices or cavities in the porous particulate matrix. One suitable form of coating is a dextrin solution which has the property of forming an impermeable film for preventing the escape of permeation of the flavoring oil.

EXAMPLE U

2-Hydroxyethyl methacrylate (100 parts) is stirred with 0.05 part t-butyl peroctoate in a nitrogen atmosphere at a temperature of 40° C. for 30 minutes. The resultant mixture is cooled to 25° C. and further 0.10 part t-butyl peroctoate is added, ethylene glycol dimethacrylate (0.1 part) being added at the same time. To this casting solution oil of peppermint, added in an amount of 10 parts. After curing and granulation, the flavored powder is used as part of a flavor releasing formulation in smoking tobaccos or "hot" beverage powders as exemplified infra.

EXAMPLE V

Distilled 2-hydroxyethyl methacrylate (100 gm) is stirred with 0.05 gm tertiary butyl peroctoate in an anaerobic atmosphere at 25°–70° C. for 14–40 minutes. The resultant mixture is cooled to 25° C. and a further 0.10 gm of tertiary butyl peroctoate is added together with 0.15 gm of ethylene glycol dimethacrylate. Oil of peppermint syrup to yield a flavored prepolylmer syrup which is suitable for storing. After curing and granulation, the flavor-carrying granules are added as a flavoring releasing component to smoking tobacco or "hot" beverage powders as set forth infra.

EXAMPLE W

A. PREPARATION OF LEMON OIL CAPSULES PREPARATION OF THE SHEEL COMPOSITION AND SOLUTION

Five hundred grams of water are heated to boil and 500 grams dextrin (National Starch and Chemical Corporation, 78-1523) is added with rapid and efficient mixing, using a closed turbine, high shear mixer (Barrington CONVERTI JET Model CJ-5B). Mixing is continued until a homogeneous solution is obtained.

B. PREPARATION OF LEMON OIL CAPSULE COMPOSITION

81 Grams of lemon oil (California cold pressed oil) is emulsified in 300 grams of the shell composition solution (A) by means of a homogenizing mixer (Barrington CONVERTI JET Model CJ-5B operated as a closed turbine unit). At the start of the operation the temperature of the matrix composition solution is 20° C. and of the lemon oil 15° C. The mixing vessel is cooled during the operation of the mixture in order to prevent a rise in the temperature and to keep the temperature below 25° C.

C. CAPSULE FORMATION AND DEHYDRATION

One thousand grams of polyethylene glycol having an average molecular weight of 400 (Union Carbide Corporation, Carbowax 400) and at a temperature of about 25° C. is placed in a vessel equipped with a homogenizing mixer (Barrington CONVERTI JET Model CJ-5B operated as an open turbine unit). One hundred grams of the lemon oil capsule composition (B) is introduced into the polyethylene glycol in a thin stream with steady medium speed operation of the mixer (about 1,500 rpm shaft speed). By the action of the mixer, the lemon oil emulsion is broken up into coarse liquid particles, which in contact with the polyethylene glycol, are rapidly converted into gel particles and finally into virtually anhydrous capsule granules.

The capsule granules are separated from the excess polyethylene glycol by means of a basket centrifuge and added to chewing gum, toothpaste, chewable vitamin tablets and chewing tobacco as set forth infra.

The following examples are given to illustrate embodiments of the invention as it is presently preferred to practice it. It will be understood that these examples are illustrative, and the invention is not to be considered as restricted thereto except as indicated in the appended claims.

EXAMPLE I

The following mixture is prepared:

| Ingredient | Parts by Weight |
| --- | --- |
| Liquid Flavor Composition of Example A | 48.4 |
| KLUCEL ® type EF (brand of hydroxypropyl cellulose manufactured by Hercules Corporation of Wilmington, Delaware having a molecular weight of about 50,000 and having a viscosity defined according to FIG. 2.) | 3.2 |

The KLUCEL ® EF is dispersed in the viscous liquid flavor composition of Example A with vigorous stirring, thereby resulting in a viscous liquid. 48.4 Parts by weight of the powder flavor composition of Example D is then blended into the said viscous liquid, with stirring at 25° C. for a period of 30 minutes, resulting in a thixotropic sustained release flavor paste.

EXAMPLE II

The following mixture is prepared:

| Ingredient | Parts by Weight |
| --- | --- |
| Liquid flavor composition of Example A | 26 |
| KLUCEL ® LF (manufactured by the Hercules Corporation of Wilmington, Delaware having a molecular weight of about 100,000 and a viscosity defined according to FIG. 2.) | 9 |

The KLUCEL® LF is dispersed in the liquid flavor composition of Example A with vigorous stirring, thereby resulting in a viscous liquid. 65 Parts by weight of the powder flavor compositions of Example D is then blended into the said viscous liquid, with stirring at 25° C. for a period of 30 minutes resulting in a dry, free flowing sustained release flavor powder.

EXAMPLE III

The following mixture is prepared:

| Ingredient | Parts by Weight |
|---|---|
| Peppermint Oil | 47.25 |
| Propylene glycol | 0.50 |
| KLUCEL® JF (brand of hydroxypropyl cellulose manufactured by the Hercules Corporation of Wilmington, Delaware having a molecular weight of about 120,000 and a viscosity defined according to FIG. 2.) | 5.00 |

The KLUCEL® JF is dispersed in the peppermint oil with vigorous stirring, thereby resulting in a viscous liquid. 47.25 Parts by weight of the powder flavor composition of Example K is then blended into the said viscous liquid, with stirring at 25° C. for a period of 30 minutes resulting in a thixotropic sustained release flavor paste.

EXAMPLE IV

The following mixture is prepared:

| Ingredient | Parts by Weight |
|---|---|
| Peppermint oil | 20 |
| Propylene glycol | 1.00 |
| KLUCEL® GF (brand of hydroxypropyl cellulose manufactured by Hercules Corp. of Wilmington, Delaware having a molecular weight of about 300,000 and a viscosity defined according to FIG. 2.) | 9.00 |

The KLUCEL® GF is dispersed in the peppermint oil with vigorous stirring, thereby resulting in a viscous liquid. 71 Parts by weight of the powder flavor composition of Example L is then blended into the said viscous liquid, with stirring at 25° C. for a period of 30 minutes resulting in a dry, free flowing sustained release flavor powder.

EXAMPLE V

The following mixture is prepared:

| Ingredient | Parts by Weight |
|---|---|
| Liquid flavor composition of Example B | 20 |
| Propylene glycol | 1.00 |
| KLUCEL® MF (brand of hydroxypropyl cellulose produced by the Hercules Corp. of Wilmington, Delaware having a molecular weight of about 700,000 and a viscosity defined according to FIG. 2.) | 9.00 |

The KLUCEL® MG is dispersed in the liquid flavor composition of Example B with vigorous stirring, thereby resulting in a viscous liquid. 65 Parts by weight of the powder flavor composition of Example E is then blended into the said viscous liquid, with stirring at 25° C. for a period of 30 minutes resulting in a dry, free flowing sustained release flavor powder.

EXAMPLE VI

The following mixture is prepared:

| Ingredient | Parts by Weight |
|---|---|
| Liquid flavor composition of Example C | 48.4 |
| Ethyl Cellulose | 3.2 |
| KLUCEL® type HF (brand of hydroxypropyl cellulose manufactured by the Hercules Corporation of Wilmington, Delaware having a molecular weight of about 800,000 and a viscosity defined according to FIG. 2) | 2.0 |

The ethyl cellulose and hydroxypropyl cellulose are intimately admixed. The intimate admixture of ethyl cellulose and hydroxypropyl cellulose is dispersed in the liquid flavor composition of Example C with vigorous stirring thereby resulting in a viscous liquid. 48.4 Parts by weight of the powder flavor composition of Example F is then blended into the said viscous liquid, with stirring at 25° C. for a period of 30 minutes resulting in a thixotropic sustained release flavor paste.

EXAMPLE VII

The following Mixture is prepared:

| Ingredient | Parts by Weight |
|---|---|
| Oil of wintergreen | 47.25 |
| Propylene glycol | 0.50 |
| KLUCEL® HF (brand of hydroxypropyl cellulose produced by the Hercules Corporation of Wilmington, Delaware having a molecular weight of about 800,000 and a viscosity defined according to FIG. 2) | 5.00 |

The KLUCEL® HF is dispersed in the oil of wintergreen with vigorous stirring, thereby resulting in a viscous liquid. 47.25 Parts by weight of the powder flavor composition of Example M is then blended into the said viscous liquid, with stirring at 25° C. for a period of 30 minutes resulting in a thixotropic sustained release flavor paste.

EXAMPLE VIII

The following mixture is prepared:

| Ingredient | Parts by Weight |
|---|---|
| Liquid flavor composition of Example A | 26 |
| Propylene glycol | 1 |
| KLUCEL® HF (brand of hydroxypropyl cellulose produced by the Hercules Corporation of Wilmington, Delaware having a molecular weight of about 800,000 and a viscosity defined according to FIG. 2) | 9 |

The KLUCEL® HF is dispersed in the liquid flavor composition of Example A with vigorous stirring, thereby resulting in a viscous liquid. 65 Parts by weight of the powdered flavor composition of Example N is then blended into the said viscous liquid, with stirring at

EXAMPLE IX

The following mixture is prepared:

| Ingredient | Parts by Weight |
|---|---|
| Liquid flavor composition of Example B | 48.4 |
| Propylene glycol | 2 |
| KLUCEL ® HF (brand of hydroxypropyl cellulose produced by the Hercules Corporation of Wilmington, Delaware having a molecular weight of about 800,000 and a viscosity defined according to FIG. 2) | 3.4 |

The KLUCEL ® HF is dispersed in the liquid flavor composition of Example B with vigorous stirring, thereby resulting in a viscous liquid. 48.4 Parts by weight of the powder flavor composition of Example O is then blended into the said viscous liquid, with stirring at 25° C. for a period of 30 minutes resulting in a thixotropic sustained release flavor paste.

EXAMPLE X

The following mixture is prepared:

| Ingredient | Parts by Weight |
|---|---|
| Liquid flavor composition of Example C | 48.4 |
| Propylene Glycol | 5 |
| Ethyl Cellulose | 4.1 |
| KLUCEL ® type MF (brand of hydroxypropyl cellulose produced by the Hercules Corporation of Wilmington, Delaware having a molecular weight of about 700,000 and a viscosity defined according to FIG. 2) | 0.5 |

An intimate admixture is made of the ethyl cellulose and hydroxypropyl cellulose. The mixture of ethyl cellulose and hydroxypropyl cellulose is dispersed in the liquid flavor composition of Example C with vigorous stirring thereby resulting in a viscous liquid. 48.4 Parts by weight of the powder flavor composition of Example P is then blended into the said viscous liquid, with stirring at 25° C. for a period of 30 minutes resulting in a thixotropic sustained release flavor paste.

EXAMPLE XI

The following mixture is prepared:

| Ingredient | Parts by Weight |
|---|---|
| Orange oil | 48.4 |
| KLUCEL ® GF (brand of hydroxypropyl cellulose produced by the Hercules Corporation of Wilmington, Delaware having a molecular weight of about 300,000 and a viscosity defined according to FIG. 2) | 3.2 |

The KLUCEL ® GF is dispersed in the orange oil with vigorous stirring, thereby resulting in a viscous liquid. 48.4 Parts by weight of the powder flavor composition of Example Q is then blended into the said viscous liquid, with stirring at 25° C. for a period of 30 minutes resulting in a thixotropic sustained release flavor pastae.

EXAMPLE XII

The following mixture is prepared:

| Ingredient | Parts by Weight |
|---|---|
| Liquid flavor composition of Example A | 20 |
| Propylene glycol | 2 |
| KLUCEL ® GF (brand of hydroxypropyl cellulose produced by the Hercules Corporation of Wilmington, Delaware having a molecular weight of about 300,000 and a viscosity defined according to FIG. 2) | 4.2 |
| Ethyl cellulose | 1.0 |

The KLUCEL ® GF and ethyl cellulose is dispersed in the liquid flavor composition of Example A with vigorous stirring, thereby resulting in a viscous liquid. 70 Parts by weight of the powder flavor composition of Example R is then blended into the said viscous liquid, with stirring at 25° C. for a period of 30 minutes resulting in a dry, free flowing sustained release flavor powder.

The KLUCEL ® GF and ethyl cellulose is dispersed in the liquid flavor composition of Example A with vigorous stirring, thereby resulting in a viscous liquid. 70 Parts by weight of the powder flavor composition of Example R is then blended into said viscous liquid, with stirring at 25° C. for a period of 30 minutes resulting in a dry, free flowing sustained release flavor powder.

EXAMPLE XIII

The following mixture is prepared:

| Ingredient | Parts by Weight |
|---|---|
| Liquid flavor composition of Example A | 20 |
| Propylene glycol | 1 |
| KLUCEL ® GF (brand of hydroxypropyl cellulose produced by the Hercules Corporation of Wilmington, Delaware having a molecular weight of about 300,000 and a viscosity | 3 |
| Ethyl cellulose | 3 |

The KLUCEL ® GF and ethyl cellulose are dispersed in the liquid flavor composition of Example A with vigorous stirring, thereby resulting in a viscous liquid. 65 Parts by weight of the powder flavor composition of Example R is then blended into the said viscous liquid with stirring at 25° C. for a period of 30 minutes resulting in a dry, free flowing sustained release flavor powder.

EXAMPLE XIV

The following mixture is prepared:

| Ingredient | Parts by Weight |
|---|---|
| Liquid flavor composition of Example B | 48.4 |
| Propylene glycol | 2 |
| KLUCEL ® GF (brand of hydroxypropyl cellulose produced by the Hercules Corporation of Wilmington, Delaware having a molecular weight of about 300,000 and a viscosity defined according to FIG. 2) | 3.2 |

-continued

| Ingredient | Parts by Weight |
|---|---|
| Ethyl cellulose | 1.5 |

The KLUCEL ® GF and ethyl cellulose is dispersed in the liquid flavor composition of Example B with vigorous stirring, thereby resulting in a viscous liquid. 48.4 Parts by weight of the powder flavor composition of Example S is then blended into the said viscous liquid, with stirring at 25° C. for a period of 30 minutes resulting in a thixotropic sustained release flavor paste.

EXAMPLE XV

The following mixture is prepared:

| Ingredient | Parts by Weight |
|---|---|
| Liquid flavor composition of Example C | 18 |
| Propylene glycol | 1 |
| KLUCEL ® GF (brand of hydroxypropyl cellulose produced by the Hercules Corporation of Wilmington, Delaware having a molecular weight of about 300,000 and a viscosity defined according to FIG. 2) | 3 |
| Ethyl cellulose | 1 |

The KLUCEL ® GF and ethyl cellulose is dispersed in the liquid flavor composition of Example C with vigorous stirring, thereby resulting in a viscous liquid. 62 Parts by weight of the powder flavor composition of Example T is then blended into the said viscous liquid, with stirring at 25° C. for a period of 30 minutes resulting in a dry, free flowing sustained release flavor powder.

EXAMPLE XVI

The following mixture is prepared:

| Ingredient | Parts by Weight |
|---|---|
| Peppermint oil | 48.4 |
| Propylene glycol | 2 |
| KLUCEL ® GF (brand of hydroxypropyl cellulose produced by the Hercules Corporation of Wilmington, Delaware having a molecular weight of about 300,000 and a viscosity defined according to FIG. 2) | 3.8 |

The KLUCEL ® GF is dispersed in the peppermint oil with vigorous stirring, thereby resulting in a viscous liquid. 48.4 Parts by weight of the powder flavor composition in Example U is then blended into the said viscous liquid, with stirring at 25° C. for a period of 30 minutes resulting in a thixotropic sustained release flavor paste.

EXAMPLE VII

The following mixture is prepared:

| Ingredient | Parts by Weight |
|---|---|
| Peppermint oil | 21 |
| Propylene glycol | 1.0 |
| KLUCEL ® GF (brand of hydroxypropyl cellulose produced by the Hercules Corporation of Wilmington, Delaware having a molecular weight | 2.0 |

-continued

| Ingredient | Parts by Weight |
|---|---|
| of about 300,000 and a viscosity defined according to FIG. 2) | |
| Ethyl cellulose | 3.2 |

The KLUCEL ® GF and ethyl cellulose is dispersed in the peppermint oil with vigorous stirring, thereby resulting in a viscous liquid. 65 Parts by weight of the powder flavor composition of Example V is then blended into the said viscous liquid, with stirring at 25° C. for a period of 30 minutes in a dry, free flowing sustained release flavor powder.

EXAMPLE XVIII

The following mixture is prepared:

| Ingredient | Parts by Weight |
|---|---|
| Liquid flavor composition of Example B | 52 |
| Propylene glycol | 1 |
| KLUCEL ® GF (brand of hydroxypropyl cellulose produced by the Hercules Corporation of Wilmington, Delaware having a molecular weight of about 300,000 and a viscosity defined according to FIG. 2) | 3.8 |
| Ethyl cellulose | 2.2 |

The KLUCEL ® GF and ethyl cellulose is dispersed in the liquid flavor composition of Example B with vigorous stirring, thereby resulting in a viscous liquid. 44 Parts by weight of the powder flavor composition of Example W is then blended into the said viscous liquid, with stirring at 25° C. for a period of 30 minutes resulting in a thixotropic sustained release flavor paste.

EXAMPLE XIX

The following mixture is prepared:

| Ingredient | Parts by Weight |
|---|---|
| Liquid flavor composition of Example A | 48.4 |
| Propylene glycol | 3 |
| KLUCEL ® GF (brand of hydroxypropyl cellulose produced by the Hercules Corporation of Wilmington, Delaware having a molecular weight of about 300,000 and a viscosity defined according to FIG. 2) | 5.2 |

The KLUCEL ® GF and is dispersed in the liquid flavor composition of Example A with vigorous stirring, thereby resulting in a viscous liquid. 48.4 Parts by weight of the powder flavor composition of Example G is then blended into the said viscous liquid, with stirring at 25° C. for a period of 50 minutes resulting in a thixotropic sustained release flavor paste.

EXAMPLE XX

The following mixture is prepared:

| Ingredient | Parts by Weight |
|---|---|
| Liquid flavor composition of Example B | 25 |
| Propylene glycol | 2 |
| KLUCEL ® GF (brand of hydroxypropyl cellulose produced by the | 10 |

-continued

| Ingredient | Parts by Weight |
| --- | --- |
| Hercules Corporation of Wilmington, Delaware having a molecular weight of about 300,000 and a viscosity defined according to FIG. 2) | |
| Ethyl cellulose | 4 |

The KLUCEL® GF and ethyl cellulose is dispersed in the liquid flavor composition of Example B with vigorous stirring, thereby resulting in a viscous liquid. 65 Parts by weight of the powder flavor composition of Example H is then blended into the said viscous liquid, with stirring at 40° C. for a period of 100 minutes resulting in a dry, free flowing sustained release flavor paste.

EXAMPLE XXI

The following mixture is prepared:

| Ingredient | Parts by Weight |
| --- | --- |
| Liquid flavor composition of Example C | 25 |
| Propylene glycol | 1 |
| KLUCEL® GF (brand of hydroxypropyl cellulose produced by the Hercules Corporation of Wilmington, Delaware having a molecular weight of about 300,000 and a viscosity defined according to FIG. 2) | 3 |
| Ethyl cellulose | 8 |

The KLUCEL® GF and ethyl cellulose is dispersed in the liquid flavor composition of Example C with vigorous stirring, thereby resulting in a viscous liquid. 65 Parts by weight of the powder flavor composition of Example J is then blended into the said viscous liquid, with stirring at 25° C. for a period of 30 minutes resulting in a dry, free flowing sustained release flavor paste.

EXAMPLE XXII

CHEWING GUM 100 parts by weight of chicle are mixed with 4 parts by weight of the flavor prepared in accordance with Example I. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting cherry flavor.

EXAMPLE XXIII

CHEWING GUM 100 parts by weight of chicle are mixed with 18 parts by weight of the flavor prepared in accordance with Example II. 300 parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting cherry flavor.

EXAMPLE XXIV

CHEWING GUM 100 parts by weight of chicle are mixed with 4 parts by weight of the flavor prepared in accordance with Example III. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting peppermint flavor.

EXAMPLE XXV

CHEWING GUM 100 parts by weight of chicle are mixed with 18 parts by weight of the flavor prepared in accordance with Example IV. 300 parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting peppermint flavor.

EXAMPLE XXVI

CHEWING GUM 100 parts by weight of chicle are mixed with 4 parts by weight of the flavor prepared in accordance with Example V. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting lemon flavor.

EXAMPLE XXVII

CHEWING GUM 100 parts by weight of chicle are mixed with 18 parts by weight of the flavor prepared in accordance with Example VI. 300 parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting lime flavor.

EXAMPLE XXVIII

CHEWING GUM 100 parts by weight of chicle are mixed with 4 parts by weight of the flavor prepared in accordance with Example VII. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting wintergreen flavor.

EXAMPLE XXIX

CHEWING GUM 100 parts by weight of chicle are mixed with 18 parts by weight of the flavor prepared in accordance with Example VIII. 300 parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting cherry flavor.

EXAMPLE XXX

CHEWING GUM 100 parts by weight of chicle are mixed with 4 parts by weight of the flavor prepared in accordance with Example IX. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting lemon flavor.

EXAMPLE XXXI

CHEWING GUM 100 parts by weight of chicle are mixed with 18 parts by weight of the flavor prepared in accordance with Example X. 300 parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting lime flavor.

EXAMPLE XXXII

CHEWING GUM 100 parts by weight of chicle are mixed with 4 parts by weight of the flavor prepared in accordance with Example XI. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting orange flavor.

EXAMPLE XXXIII

CHEWING GUM 100 parts by weight of chicle are mixed with 18 parts by weight of the flavor prepared in accordance with Example XII. 300 parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting cherry flavor.

EXAMPLE XXXIV

CHEWING GUM 100 parts by weight of chicle are mixed with 4 parts by weight of the flavor prepared in accordance with Example XIII. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting cherry flavor.

EXAMPLE XXXV

CHEWING GUM 100 parts by weight of chicle are mixed with 18 parts by weight of the flavor prepared in accordance with Example XIV. 300 parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting lemon flavor.

EXAMPLE XXXVI

CHEWING GUM 100 parts by weight of chicle are mixed with 4 parts by weight of the flavor prepared in accordance with Example XV. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting lime flavor.

EXAMPLE XXXVII

CHEWING GUM 100 parts by weight of chicle are mixed with 18 parts by weight of the flavor prepared in accordance with Example XVI. 300 parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths for 3 inches each. On chewing, the chewing gum has a pleasant long lasting peppermint flavor.

EXAMPLE XXXVIII

CHEWING GUM 100 parts by weight of chicle are mixed with 4 parts by weight of the flavor prepared in accordance with Example XVII. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting peppermint flavor.

EXAMPLE XXXIX

CHEWING GUM 100 parts by weight of chicle are mixed with 18 parts by weight of the flavor prepared in accordance with Example XVIII. 300 parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are out into lengths of 3 inches each. On chewing, the chewing gum has a pleasant long lasting lemon flavor.

EXAMPLE XL

CHEWING GUM 100 parts by weight of chicle are mixed with 4 parts by weight of the flavor prepared in accordance with Example XIX. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting cherry flavor.

EXAMPLE XLI

CHEWING GUM 100 parts by weight of chicle are mixed with 18 parts by weight of the flavor prepared in accordance with Example XX. 300 parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting lemon flavor.

EXAMPLE XLII

CHEWING GUM 100 parts by weight of chicle are mixed with 4 parts by weight of the flavor prepared in accordance with Example XXI. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting lime flavor.

A taste test is made to compare the chewing gum products of this invention of Examples XXII-XLII inclusive with (i) standard chewing gum containing the same total amount of flavor in unfixed form and (ii) chewing gum containing the same total amount of flavor without the hydroxypropyl cellulose and with each flavor ingredient (fixed and unfixed) added to the chicle separately rather than in a blend. During the test, 1.0 inch ×3.0 inch ×0.1 inch slabs of each gum are separately chewed and the following noted: Time and intensity of initial flavor, extent of flavor burst, duration of interesting flavor level, and approximate total time during which flavor is available. In these tests, the rating of flavor intensity is measured by the person chewing, on a scale ranging from 0 to 10, the level of 1 indicating threshold flavor intensity just discernible to the taste, and a level of 10 indicating a maximum intensity above which the sensation originating in flavor is unpleasant.

The commercially available standard (i) containing unfixed flavor is chicle is characterized by initial indication of flavor at a level of 1 after about 7-8 seconds. Intensity rises to 3 at about 15 seconds, and thereafter at a slower rate to a level of 6 at about 60 seconds. At this point, flavor intensity drops off to 3 after about 90 seconds. At about 2 minutes, the flavor intensity is at the uninteresting low level of 1.5. After 4 minutes of chewing, the flavor drops below the threshold value of 1, and the standard gum (i) is flat and lifeless.

The standard (ii) containing flavor in both fixed and unfixed form but without the hydroxypropyl cellulose and with each flavor ingredient (fixed and unfixed) added to the chicle separate rather than in a blend, is characterized by initial indication of flavor at a level of 3 after 7-8 seconds with intensity rising to 6 to about 20 seconds and thereafter a slower rate at a level of 7 at about 60 seconds. At that point, the flavor intensity drops off to about 5 after about 90 seconds. At about 4 minutes, the flavor intensity is at the uninteresting level of 1.5. After 8 minutes of chewing, the flavor drops below the threshold value of 1 and the standard gum (ii) is flat and lifeless.

Samples prepared in accordance with the invetion as set forth in Examples XXII-XLII, supra, are found to have an initial flavor liberation which occurs substantially immediately (at about 0.25 seconds) i.e. more quickly than does that of the standard or (i) or (ii), and which is at a higher level than that of either standard. The flavor or intensity of the chewing gum product of this invention continuously rises to a high level which is four fold that of the maximum level reached by the standard (i) and twice that of the maximum level reached by the standard (ii) and it remains at this high level for a total period of time which is four fold the total flavor perception time of the standard (i) and twice the total flavor perception time of the standard (ii). Under preferred conditions, flavor liberation is apparent for a time which approaches 20 minutes. During the entire chewing period, which is typically 2-4 times as long as the chewinperiod of either standard chewing gum, the flavor of the product of this invention may be found to be rich, full-bodied and substantially true in character.

It will be apparent to the person making the chewing test that the chewing gum samples prepared in accordance with this invention are eminently superior to the samples containing the same amount of flavoring oil in unfixed form alone or the chewing gum containing the same total amount of flavor without the hydroxypropyl cellulose and with each flavor ingredient (fixed and unfixed) added to the chicle separately rather than in a blend. The extended flavor perception time, early flavor release, true flavor character, and high degree of released flavor make this new product superior.

EXAMPLE XLIII

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Flouride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example I |
| 100.00 (Total) | |

PROCEDURE

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant cherry flavor, of constant strong intensity throughout said procedure (1–1.5 minutes).

EXAMPLE XLIV

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Flouride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example II |
| 100.00 (Total) | |

PROCEDURE

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant cherry flavor, of constant strong intensity throughout said procedure (1–1.5 minutes).

EXAMPLE XLV

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Flouride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example III |
| 100.00 (Total) | |

PROCEDURE

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant peppermint flavor, of constant strong intensity throughout said procedure (1–1.5 minutes).

EXAMPLE XLVI

TOOTHPASTE FORMULATION

The following separate groups of ingredients are prepared:

| Parts by Weight | Ingredient |
| --- | --- |
| Group "A" | |
| 30.200 | Glycerin |
| 15.325 | Distilled Water |
| .100 | Sodium Benzoate |
| .125 | Saccharin Sodium |
| .400 | Stannous Flouride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example IV |
| 100.00 (Total) | |

PROCEDURE

| | |
| --- | --- |
| 1. | The ingredients in Group "A" are stirred and heated in a steam jacketed kettle to 160° F. |
| 2. | Stirring is continued for an additional three to five minutes to form a homogeneous gel. |
| 3. | The powders of Group "B" are added to the gel, while mixing until a homogeneous paste is formed. |
| 4. | With stirring, the flavor of "D" is added and lastly the sodium n-lauroyl sarcosinate. |
| 5. | The resultant slurry is then blended for one hour. The completed paste is then transferred to a three roller mill and then homogenized, and finally tubed. |

The resulting toothpaste when used in a normal toothbrushing procedure yields a pleasant peppermint flavor, of constant strong intensity throughout said procedure (1–1.5 minutes).

EXAMPLE XLVII

TOOTHPASTE FORMULATION

The following separate groups of ingredients are prepared:

| Parts by Weight | Ingredient |
| --- | --- |
| Group "A" | |
| 30.200 | Glycerin |
| 15.325 | Distilled Water |
| .100 | Sodium Benzoate |
| .125 | Saccharin Sodium |
| .400 | Stannous Flouride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example V |
| 100.00 (Total) | |

PROCEDURE

| | |
| --- | --- |
| 1. | The ingredients in Group "A" are stirred and heated in a steam jacketed kettle to 160° F. |
| 2. | Stirring is continued for an additional three to five minutes to form a homogeneous gel. |
| 3. | The powders of Group "B" are added to the gel, while mixing until a homogeneous paste is formed. |
| 4. | With stirring, the flavor of "D" is added and lastly the sodium n-lauroyl sarcosinate. |
| 5. | The resultant slurry is then blended for one hour. The completed paste is then transferred to a three roller mill and then homogenized, and finally tubed. |

The resulting toothpaste when used in a normal toothbrushing procedure yields a pleasant lemon flavor, of constant strong intensity throughout said procedure (1–1.5 minutes).

EXAMPLE XLVIII

TOOTHPASTE FORMULATION

The following separate groups of ingredients are prepared:

| Parts by Weight | Ingredient |
| --- | --- |
| Group "A" | |
| 30.200 | Glycerin |
| 15.325 | Distilled Water |
| .100 | Sodium Benzoate |
| .125 | Saccharin Sodium |
| .400 | Stannous Flouride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example VI |
| 100.00 (Total) | |

PROCEDURE

| | |
| --- | --- |
| 1. | The ingredients in Group "A" are stirred and heated in a steam jacketed kettle to 160° F. |
| 2. | Stirring is continued for an additional three to five minutes to form a homogeneous gel. |
| 3. | The powders of Group "B" are added to the gel, while mixing until a homogeneous paste is formed. |
| 4. | With stirring, the flavor of "D" is added and lastly the sodium n-lauroyl sarcosinate. |
| 5. | The resultant slurry is then blended for one hour. The completed paste is then transferred to a three roller mill and then homogenized, and finally tubed. |

The resulting toothpaste when used in a normal toothbrushing procedure yields a pleasant lime flavor, of constant strong intensity throughout said procedure (1–1.5 minutes).

EXAMPLE XLIX

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Flouride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example VII |
| 100.00 (Total) | |

PROCEDURE

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant wintergreen flavor, of constant strong intensity throughout said procedure (1-1.5 minutes).

EXAMPLE L

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Flouride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example VIII |
| 100.000 (Total) | |

PROCEDURE

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant cherry flavor, of constant strong intensity throughout said procedure (1-1.5 minutes).

EXAMPLE LI

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Flouride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example IX |
| 100.00 (Total) | |

PROCEDURE

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant lemon flavor, of constant strong intensity throughout said procedure (1-1.5 minutes).

EXAMPLE LII

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Flouride |
| Group "B" | |
| 12.500 | Calcium Carbonate |

| Parts by Weight | Ingredient |
|---|---|
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example X |
| 100.00 (Total) | |

PROCEDURE

| | |
|---|---|
| 1. | The ingredients in Group "A" are stirred and heated in a steam jacketed kettle to 160° F. |
| 2. | Stirring is continued for an additional three to five minutes to form a homogeneous gel. |
| 3. | The powders of Group "B" are added to the gel, while mixing until a homogeneous paste is formed. |
| 4. | With stirring, the flavor of "D" is added and lastly the sodium n-lauroyl sarcosinate. |
| 5. | The resultant slurry is then blended for one hour. The completed paste is then transferred to a three roller mill and then homogenized, and finally tubed. |

The resulting toothpaste when used in a normal toothbrushing procedure yields a pleasant lime flavor, of constant strong intensity throughout said procedure (1–1.5 minutes).

LIII

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XI |
| 100.00 (Total) | |

PROCEDURE

| | |
|---|---|
| 1. | The ingredients in Group "A" are stirred and heated in a steam jacketed kettle to 160° F. |
| 2. | Stirring is continued for an additional three to five minutes to form a homogeneous gel. |
| 3. | The powders of Group "B" are added to the gel, while mixing until a homogeneous paste is formed. |
| 4. | With stirring, the flavor of "D" is added and lastly the sodium n-lauroyl sarcosinate. |
| 5. | The resultant slurry is then blended for one hour. The completed paste is then transferred to a three roller mill and then homogenized, and finally tubed. |

The resulting toothpaste when used in a normal toothbrushing procedure yields a pleasant orange flavor, of constant strong intensity throughout said procedure (1–1.5 minutes).

EXAMPLE LIV

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XII |
| 100.00 (Total) | |

PROCEDURE

| | |
|---|---|
| 1. | The ingredients in Group "A" are stirred and heated in a steam jacketed kettle to 160° F. |
| 2. | Stirring is continued for an additional three to five minutes to form a homogeneous gel. |
| 3. | The powders of Group "B" are added to the gel, while mixing until a homogeneous paste is formed. |
| 4. | With stirring, the flavor of "D" is added and lastly the sodium n-lauroyl sarcosinate. |
| 5. | The resultant slurry is then blended for one hour. The completed paste is then transferred to a three roller mill and then homogenized, and finally tubed. |

The resulting toothpaste when used in a normal toothbrushing procedure yields a pleasant cherry flavor, of constant strong intensity throughout said procedure (1–1.5 minutes).

EXAMPLE LV

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XIII |
| 100.00 (Total) | |

PROCEDURE

| | |
|---|---|
| 1. | The ingredients in Group "A" are stirred and heated in a steam jacketed kettle to 160° F. |
| 2. | Stirring is continued for an additional three to five minutes to form a |

|   |   |
|---|---|
|   | homogeneous gel. |
| 3. | The powders of Group "B" are added to the gel, while mixing until a homogeneous paste is formed. |
| 4. | With stirring, the flavor of "D" is added and lastly the sodium n-lauroyl sarcosinate. |
| 5. | The resultant slurry is then blended for one hour. The completed paste is then transferred to a three roller mill and then homogenized, and finally tubed. |

The resulting toothpaste when used in a normal toothbrushing procedure yields a pleasant cherry flavor, of constant strong intensity throughout said procedure (1–1.5 minutes).

EXAMPLE LVI

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Flouride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XIV |
| 100.00 (Total) | |
| PROCEDURE | |
| 1. | The ingredients in Group "A" are stirred and heated in a steam jacketed kettle to 160° F. |
| 2. | Stirring is continued for an additional three to five minutes to form a homogeneous gel. |
| 3. | The powders of Group "B" are added to the gel, while mixing until a homogeneous paste is formed. |
| 4. | With stirring, the flavor of "D" is added and lastly the sodium n-lauroyl sarcosinate. |
| 5. | The resultant slurry is then blended for one hour. The completed paste is then transferred to a three roller mill and then homogenized, and finally tubed. |

The resulting toothpaste when used in a normal toothbrushing procedure yields a pleasant lemon flavor, of constant strong intensity throughout said procedure (1–1.5 minutes).

EXAMPLE LVII

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XV |
| 100.00 (Total) | |
| PROCEDURE | |
| 1. | The ingredients in Group "A" are stirred and heated in a steam jacketed kettle to 160° F. |
| 2. | Stirring is continued for an additional three to five minutes to form a homogeneous gel. |
| 3. | The powders of Group "B" are added to the gel, while mixing until a homogeneous paste is formed. |
| 4. | With stirring, the flavor of "D" is added and lastly the sodium n-lauroyl sarcosinate. |
| 5. | The resultant slurry is then blended for one hour. The completed paste is then transferred to a three roller mill and then homogenized, and finally tubed. |

The resulting toothpaste when used in a normal toothbrushing procedure yields a pleasant lime flavor, of constant strong intensity throughout said procedure (1–1.5 minutes).

EXAMPLE LVIII

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XVI |
| 100.00 (Total) | |
| PROCEDURE | |
| 1. | The ingredients in Group "A" are stirred and heated in a steam jacketed kettle to 160° F. |
| 2. | Stirring is continued for an additional three to five minutes to form a homogeneous gel. |
| 3. | The powders of Group "B" are added to the gel, while mixing until a homogeneous paste is formed. |
| 4. | With stirring, the flavor of "D" is added and lastly the sodium n-lauroyl sarcosinate. |
| 5. | The resultant slurry is then blended for one hour. The completed paste is then transferred to a three roller mill and then homogenized, and finally tubed. |

The resulting toothpaste when used in a normal toothbrushing procedure yields a pleasant peppermint flavor, of constant strong intensity throughout said procedure (1-1.5 minutes).

EXAMPLE LIX

TOOTHPASTE FORMULATION

The following separate groups of ingredients are prepared:

| Parts by Weight | Ingredient |
| --- | --- |
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XVII |
| 100.00 (Total) | |

PROCEDURE
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant peppermint flavor, of constant strong intensity throughout said procedure (1-1.5 minutes).

EXAMPLE LX

TOOTHPASTE FORMULATION

The following separate groups of ingredients are prepared:

| Parts by Weight | Ingredient |
| --- | --- |
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XVIII |
| 100.00 (Total) | |

PROCEDURE
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant lemon flavor, of constant strong intensity throughout said procedure (1-1.5 minutes).

EXAMPLE LXI

TOOTHPASTE FORMULATION

The following separate groups of ingredients are prepared:

| Parts by Weight | Ingredient |
| --- | --- |
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XIX |
| 100.00 (Total) | |

PROCEDURE
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant cherry flavor, of constant strong intensity throughout said procedure (1-1.5 minutes).

EXAMPLE LXII

TOOTHPASTE FORMULATION

The following separate groups of ingredients are prepared:

| Parts by Weight | Ingredient |
| --- | --- |
| Group "A" | |
| 30.200 | Glycerin |
| 15.325 | Distilled Water |
| .100 | Sodium Benzoate |

-continued

| | |
|---|---|
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XX |
| 100.00 (Total) | |

PROCEDURE

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant lemon flavor, of constant strong intensity throughout said procedure (1-1.5 minutes).

EXAMPLE LXIII

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XXI |
| 100.00 (Total) | |

PROCEDURE

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant lime flavor, of constant strong intensity throughout said procedure (1-1.5 minutes).

EXAMPLE LXIV

CHEWABLE VITAMIN TABLETS

The flavor material produced according to the process of Example I is added to a Chewable Vitamin Tablet Formulation at a rate of 4 gm/gm which Chewable Vitamin Tablet Formulation is prepared as follows:

In a Hobart Mixer, the following materials are blended to homogeneity:

| | Gms/1000 tablets |
|---|---|
| Vitamin C (ascorbic acid) as ascorbic acid-sodium ascorbate mixture 1:1 | 70.0 |
| Vitamin $B_1$ (thiamine mononitrate) as Rocoat thiamine mononitrate 33⅓% (Hoffmann La Roche) | 4.0 |
| Vitamin $B_2$ (riboflavin) as Rocoat riboflavin 33⅓% | 5.0 |
| Vitamin $B_6$ (pyridoxine hydrochloride) as Rocoat pyridoxine hydrochloride 33⅓% | 4.0 |
| Niacinamide as Rocoat niacinamide 33⅓% | 33.0 |
| Calcium pantothenate | 11.5 |
| Vitamin $B_{12}$ (cyanocobalamin) as Merk 0.1% in gelatin | 3.5 |
| Vitamin E (dl-alpha tocopheryl acetate) as dry Vitamin E acetate 33⅓% Roche | 6.6 |
| d-Biotin | 0.044 |
| Certified lake color | 5.0 |
| Flavor of Example I | 5.0 |
| Sweetener - sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong cherry flavor for a period of 12 minutes.

EXAMPLE LXV

CHEWABLE VITAMIN TABLETS

The flavor material produced according to the process of Example II is added to a Chewable Vitamin Tablet Formulation at a rate of 5 gm/gm which Chewable Vitamin Tablet Formulation is prepared as follows:

In a Hobart Mixer, the following materials are blended to homogeneity:

| | Gms/1000 tablets |
|---|---|
| Vitamin C (ascorbic acid) as ascorbic acid-sodium ascorbate mixture 1:1 | 70.0 |
| Vitamin $B_1$ (thiamine mononitrate) as Rocoat thiamine mononitrate 33⅓% (Hoffmann La Roche) | 4.0 |
| Vitamin $B_2$ (riboflavin) as Rocoat riboflavin 33⅓% | 5.0 |
| Vitamin $B_6$ (pyridoxine hydrochloride) as Rocoat pyridoxine hydrochloride 33⅓% | 4.0 |
| Niacinamide as Rocoat niacinamide 33⅓% | 33.0 |
| Calcium pantothenate | 11.5 |
| Vitamin $B_{12}$ (cyanocobalamin) as Merk 0.1% in gelatin | 3.5 |
| Vitamin E (dl-alpha tocopheryl acetate) as dry Vitamin E acetate 33⅓% Roche | 6.6 |
| d-Biotin | 0.044 |
| Certified lake color | 5.0 |

|  | Gms/1000 tablets |
|---|---|
| Flavor of Example II | 5.0 |
| Sweetener - sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong cherry flavor for a period of 12 minutes.

EXAMPLE LXVI

CHEWABLE VITAMIN TABLETS

The flavor material produced according to the process of Example III is added to a Chewable Vitamin Tablet Formulation at a rate of 6 gm/gm which Chewable Vitamin Tablet Formulation is prepared as follows:

In a Hobart Mixer, the following materials are blended to homogeneity:

|  | Gms/1000 tablets |
|---|---|
| Vitamin C (ascorbic acid) | 70.0 |
| as ascorbic acid-sodium ascorbate mixture 1:1 |  |
| Vitamin $B_1$ (thiamine mononitrate) |  |
| as Rocoat thiamine mononitrate 33⅓% | 4.0 |
| (Hoffman La Roche) |  |
| Vitamin $B_2$ (riboflavin) |  |
| as Rocoat riboflavin 33⅓% | 5.0 |
| Vitamin $B_6$ (pyridoxine hydrochloride) |  |
| as Rocoat pyridoxine hydrochloride 33⅓% | 4.0 |
| Niacinamide |  |
| as Rocoat niacinamide 33⅓% | 33.0 |
| Calcium pantothenate | 11.5 |
| Vitamin $B_{12}$ (cyanocobalamin) |  |
| as Merk 0.1% in gelatin | 3.5 |
| Vitamin E (dl-alpha tocopheryl acetate) |  |
| as dry Vitamin E acetate 33⅓% Roche | 6.6 |
| d-Biotin | 0.044 |
| Certified lake color | 5.0 |
| Flavor of Example III | 5.0 |
| Sweetener - sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong cherry flavor for a period of 12 minutes.

EXAMPLE LXVII

CHEWABLE VITAMIN TABLETS

The flavor material produced according to the process of Example IV is added to a Chewable Vitamin Tablet Formulation at a rate of 7 gm/gm which Chewable Vitamin Tablet Formulation is prepared as follows:

In a Hobart Mixer, the following materials are blended to homogeneity:

|  | Gms/1000 tablets |
|---|---|
| Vitamin C (ascorbic acid) | 70.0 |
| as ascorbic acid-sodium ascorbate mixture 1:1 |  |
| Vitamin $B_1$ (thiamine mononitrate) |  |
| as Rocoat thiamine mononitrate 33⅓% | 4.0 |
| (Hoffman La Roche) |  |
| Vitamin $B_2$ (riboflavin) |  |
| as Rocoat riboflavin 33⅓% | 5.0 |
| Vitamin $B_6$ (pyridoxine hydrochloride) |  |
| as Rocoat pyridoxine hydrochloride 33⅓% | 4.0 |
| Niacinamide |  |
| as Rocoat niacinamide 33⅓% | 33.0 |
| Calcium pantothenate | 11.5 |
| Vitamin $B_{12}$ (cyanocobalamin) |  |
| as Merk 0.1% in gelatin | 3.5 |
| Vitamin E (dl-alpha tocopheryl acetate) |  |
| as dry Vitamin E acetate 33⅓% Roche | 6.6 |
| d-Biotin | 0.044 |
| Certified lake color | 5.0 |
| Flavor of Example IV | 5.0 |
| Sweetener - sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong cherry flavor for a period of 12 minutes.

EXAMPLE LXVIII

CHEWABLE VITAMIN TABLETS

The flavor material produced according to the process of Example V is added to a Chewable Vitamin Tablet Formulation at a rate of 7 gm/gm which Chewable Vitamin Tablet Formulation is prepared as follows:

In a Hobart Mixer, the following materials are blended to homogeneity:

|  | Gms/1000 tablets |
|---|---|
| Vitamin C (ascorbic acid) | 70.0 |
| as ascorbic acid-sodium ascorbate mixture 1:1 |  |
| Vitamin $B_1$ (thiamine mononitrate) |  |
| as Rocoat thiamine mononitrate 33⅓% | 4.0 |
| (Hoffman La Roche) |  |
| Vitamin $B_2$ (riboflavin) |  |
| as Rocoat riboflavin 33⅓% | 5.0 |
| Vitamin $B_6$ (pyridoxine hydrochloride) |  |
| as Rocoat pyridoxine hydrochloride 33⅓% | 4.0 |
| Niacinamide |  |
| as Rocoat niacinamide 33⅓% | 33.0 |
| Calcium pantothenate | 11.5 |
| Vitamin $B_{12}$ (cyanocobalamin) |  |
| as Merk 0.1% in gelatin | 3.5 |
| Vitamin E (dl-alpha tocopheryl acetate) |  |
| as dry Vitamin E acetate 33⅓% Roche | 6.6 |
| d-Biotin | 0.044 |
| Certified lake color | 5.0 |
| Flavor of Example V | 5.0 |
| Sweetener - sodium saccharin | 1.0 |
| Magnesium stearate lubricant | 10.0 |
| Mannitol g.s. to make | 500.0 |

Preliminary tablets are prepared by slugging with flatfaced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong cherry flavor for a period of 12 minutes.

EXAMPLE LXIX

CHEWABLE VITAMIN TABLETS

The flavor material produced according to the process of Example VI is added to a Chewable Vitamin Tablet Formulation at a rate of 8 gm/gm which Chewable Vitamin Tablet Formulation is prepared as follows:

In a Hobart Mixer, the following materials are blended to homogeneity:

| | Gms/1000 tablets |
|---|---|
| Vitamin C (ascorbic acid) | 70.0 |
| as ascorbic acid-sodium ascorbate mixture 1:1 | |
| Vitamin $B_1$ (thiamine mononitrate) | |
| as Rocoat thiamine mononitrate 33⅓% | 4.0 |
| (Hoffmann La Roche) | |
| Vitamin $B_2$ (riboflavin) | |
| as Rocoat riboflavin 33⅓% | 5.0 |
| Vitamin $B_6$ (pyridoxine hydrochloride) | |
| as Rocoat pyridoxine hydrochloride 33⅓% | 4.0 |
| Niacinamide | |
| as Rocoat niacinamide 33⅓% | 33.0 |
| Calcium pantothenate | 11.5 |
| Vitamin $B_{12}$ (cyanocobalamin) | |
| as Merk 0.1% in gelatin | 3.5 |
| Vitamin E (dl-alpha tocopheryl acetate) | |
| as dry Vitamin E acetate 33⅓% Roche | 6.6 |
| d-Biotin | 0.044 |
| Certified lake color | 5.0 |
| Flavor of Example VI | 5.0 |
| Sweetener - sodium saccharin | 1.0 |
| Magnesium stearate lubricant | 10.0 |
| Mannitol g.s. to make | 500.0 |

Preliminary tablets are prepared by slugging with flatfaced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong cherry flavor for a period of 12 minutes.

EXAMPLE LXX

CHEWABLE VITAMIN TABLETS

The flavor material produced according to the process of Example VII is added to a Chewable Vitamin Tablet Formulation at a rate of 9 gm/gm which Chewable Vitamin Tablet Formulation is prepared as follows:

In a Hobart Mixer, the following materials are blended to homogeneity:

| | Gms/1000 tablets |
|---|---|
| Vitamin C (ascorbic acid) | 70.0 |
| as ascorbic acid-sodium ascorbate mixture 1:1 | |
| Vitamin $B_1$ (thiamine mononitrate) | |
| as Rocoat thiamine mononitrate 33⅓% | 4.0 |
| (Hoffmann La Roche) | |
| Vitamin $B_2$ (riboflavin) | |
| as Rocoat riboflavin 33⅓% | 5.0 |
| Vitamin $B_6$ (pyridoxine hydrochloride) | |
| as Rocoat pyridoxine hydrochloride 33⅓% | 4.0 |
| Niacinamide | |
| as Rocoat niacinamide 33⅓% | 33.0 |
| Calcium pantothenate | 11.5 |
| Vitamin $B_{12}$ (cyanocobalamin) | |
| as Merk 0.1% in gelatin | 3.5 |
| Vitamin E (dl-alpha tocopheryl acetate) | |
| as dry Vitamin E acetate 33⅓% Roche | 6.6 |
| d-Biotin | 0.044 |
| Certified lake color | 5.0 |
| Flavor of Example VII | 5.0 |
| Sweetener - sodium saccharin | 1.0 |
| Magnesium stearate lubricant | 10.0 |
| Mannitol g.s. to make | 500.0 |

Preliminary tablets are prepared by slugging with flatfaced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong cherry flavor for a period of 12 minutes.

EXAMPLE LXXI

CHEWABLE VITAMIN TABLETS

The flavor material produced according to the process of Example XI is added to a Chewable Vitamin Tablet Formulation at a rate of 10 gm/gm which Chewable Vitamin Tablet Formulation is prepared as follows:

In a Hobart Mixer, the following materials are blended to homogeneity:

| | Gms/1000 tablets |
|---|---|
| Vitamin C (ascorbic acid) | 70.0 |
| as ascorbic acid-sodium ascorbate mixture 1:1 | |
| Vitamin $B_1$ (thiamine mononitrate) | |
| as Rocoat thiamine mononitrate 33⅓% | 4.0 |
| (Hoffman La Roche) | |
| Vitamin $B_2$ (riboflavin) | |
| as Rocoat riboflavin 33⅓% | 5.0 |
| Vitamin $B_6$ (pyridoxine hydrochloride) | |
| as Rocoat pyridoxine hydrochloride 33⅓% | 4.0 |
| Niacinamide | |
| as Rocoat niacinamide 33⅓% | 33.0 |
| Calcium pantothenate | 11.5 |
| Vitamin $B_{12}$ (cyanocobalamin) | |
| as Merk 0.1% in gelatin | 3.5 |
| Vitamin E (dl-alpha tocopheryl acetate) | |
| as dry Vitamin E acetate 33⅓% Roche | 6.6 |
| d-Biotin | 0.044 |
| Certified lake color | 5.0 |
| Flavor of Example XI | 5.0 |
| Sweetener - sodium saccharin | 1.0 |
| Magnesium stearate lubricant | 10.0 |
| Mannitol g.s. to make | 500.0 |

Preliminary tablets are prepared by slugging with flatfaced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong cherry flavor for a period of 12 minutes.

EXAMPLE LXXII

CHEWABLE VITAMIN TABLETS

The flavor material produced according to the process of Example XII is added to a Chewable Vitamin Tablet Formulation at a rate of 5 gm/gm which Chewable Vitamin Tablet Formulation is prepared as follows:

In a Hobart Mixer, the following materials are blended to homogeneity:

|  | Gms/1000 tablets |
|---|---|
| Vitamin C (ascrobic acid) | 70.0 |
| as ascorbic acid-sodium ascorbate mixture 1:1 | |
| Vitamin B$_1$ (thiamine mononitrate) | |
| as Rocoat thiamine mononitrate 33⅓% | 4.0 |
| (Hoffmann La Roche) | |
| Vitamin B$_2$ (riboflavin) | |
| as Rocoat riboflavin 33⅓% | 5.0 |
| Vitamin B$_6$ (pyridoxine hydrochloride) | |
| as Rocoat pyridoxine hydrochloride 33⅓% | 4.0 |
| Niacinamide | |
| as Rocoat niacinamide 33⅓% | 33.0 |
| Calcium pantothenate | 11.5 |
| Vitamin B$_{12}$ (cyanocobalamin) | |
| as Merk 0.1% in gelatin | 3.5 |
| Vitamin E (dl-alpha tocopheryl acetate) | |
| as dry Vitamin E acetate 33⅓% Roche | 6.6 |
| d-Biotin | 0.044 |
| Certified lake color | 5.0 |
| Flavor of Example XII | 5.0 |
| Sweetener - sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong cherry flavor for a period of 12 minutes.

EXAMPLE LXXIII

CHEWABLE VITAMIN TABLETS

The flavor material produced according to the process of Example XIII is added to a Chewable Vitamin Tablet Formulation at a rate of 6 gm/gm which Chewable Vitamin Tablet Formulation is prepared as follows:

In a Hobart Mixer, the following materials are blended to homogeneity:

|  | Gms/1000 tablets |
|---|---|
| Vitamin C (ascrobic acid) | 70.0 |
| as ascorbic acid-sodium ascorbate mixture 1:1 | |
| Vitamin B$_1$ (thiamine mononitrate) | |
| as Rocoat thiamine mononitrate 33⅓% | 4.0 |
| (Hoffmann La Roche) | |
| Vitamin B$_2$ (riboflavin) | |
| as Rocoat riboflavin 33⅓% | 5.0 |
| Vitamin B$_6$ (pyridoxine hydrochloride) | |
| as Rocoat pyridoxine hydrochloride 33⅓% | 4.0 |
| Niacinamide | |
| as Rocoat niacinamide 33⅓% | 33.0 |
| Calcium pantothenate | 11.5 |
| Vitamin B$_{12}$ (cyanocobalamin) | |
| as Merk 0.1% in gelatin | 3.5 |
| Vitamin E (dl-alpha tocopheryl acetate) | |
| as dry Vitamin E acetate 33⅓% Roche | 6.6 |
| d-Biotin | 0.044 |
| Certified lake color | 5.0 |
| Flavor of Example XIII | 5.0 |
| Sweetener - sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong cherry flavor for a period of 12 minutes.

EXAMPLE LXXIV

CHEWABLE VITAMIN TABLETS

The flavor material produced according to the process of Example XVI is added to a Chewable Vitamin Tablet Formulation at a rate of 7.5 gm/gm which Chewable Vitamin Tablet Formulation is prepared as follows:

In a Hobart Mixer, the following materials are blended to homogeneity:

|  | Gms/1000 tablets |
|---|---|
| Vitamin C (ascrobic acid) | 70.0 |
| as ascorbic acid-sodium ascorbate mixture 1:1 | |
| Vitamin B$_1$ (thiamine mononitrate) | |
| as Rocoat thiamine mononitrate 33⅓% | 4.0 |
| (Hoffman La Roche) | |
| Vitamin B$_2$ (riboflavin) | |
| as Rocoat riboflavin 33⅓% | 5.0 |
| Vitamin B$_6$ (pyridoxine hydrochloride) | |
| as Rocoat pyridoxine hydrochloride 33⅓% | 4.0 |
| Niacinamide | |
| as Rocoat niacinamide 33⅓% | 33.0 |
| Calcium pantothenate | 11.5 |
| Vitamin B$_{12}$ (cyanocobalamin) | |
| as Merk 0.1% in gelatin | 3.5 |
| Vitamin E (dl-alpha tocopheryl acetate) | |
| as dry Vitamin E acetate 33⅓% Roche | 6.6 |
| d-Biotin | 0.044 |
| Certified lake color | 5.0 |
| Flavor of Example XVI | 5.0 |
| Sweetener - sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong cherry flavor for a period of 12 minutes.

EXAMPLE LXXV

CHEWING TOBACCO

Onto 100 pounds of tobacco for chewing (85 percent Wisconsin leaf and 15 percent Pennsylvania leaf) the following casing is sprayed at a rate of 30 percent:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example XI | 0.4 |

The resultant product is redried to a moisture content of 20 percent. On chewing, this tobacco has an excellent substantially consistent, long-lasting orange (20 minutes) nuance in conjunction with the main fruity tobacco note.

EXAMPLE LXXVI

CHEWING TOBACCO

Onto 100 pounds of tobacco for chewing (85 percent Wisconsin leaf and 15 percent Pennsylvania leaf) the following casing is sprayed at a rate of 30 percent:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example XI | 0.4 |

The resultant product is redried to a moisture content of 20 percent. On chewing, this tobacco has an excellent substantially consistent, long-lasting orange (20 minutes) nuance in conjunction with the main fruity tobacco note.

EXAMPLE LXXVII

CHEWING TOBACCO

Onto 100 pounds of tobacco for chewing (85 percent Wisconsin leaf and 15 percent Pennsylvania leaf) the following casing is sprayed at a rate of 30 percent:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example XI | 0.4 |

The resultant product is redried to a moisture content of 20 percent. On chewing, this tobacco has an excellent substantially consistent, long-lasting orange (20 minutes) nuance in conjunction with the main fruity tobacco note.

EXAMPLE LXXVIII

CHEWING TOBACCO

Onto 100 pounds of tobacco for chewing (85 percent Wisconsin leaf and 15 percent Pennsylvania leaf) the following casing is sprayed at a rate of 30 percent:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example I | 0.4 |

The resultant product is redried to a moisture content of 20 percent. On chewing, this tobacco has an excellent substantially consistent, long-lasting cherry (20 minutes) nuance in conjunction with the main fruity tobacco note.

EXAMPLE LXXIX

CHEWING TOBACCO

Onto 100 pounds of tobacco for chewing (85 percent Wisconsin leaf and 15 percent Pennsylvania leaf) the following casing is sprayed at a rate of 30 percent:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example II | 0.4 |

The resultant product is redried to a moisture content of 20 percent. On chewing, this tobacco has an excellent substantially consistent, long-lasting cherry (20 minutes) nuance in conjunction with the main fruity tobacco note.

EXAMPLE LXXX

CHEWING TOBACCO

Onto 100 pounds of tobacco for chewing (85 percent Wisconsin leaf and 15 percent Pennsylvania leaf) the following casing is sprayed at a rate of 30 percent:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example VIII | 0.4 |

The resultant product is redried to a moisture content of 20 percent. On chewing, this tobacco has an excellent substantially consistent, long-lasting cherry (20 minutes) nuance in conjunction with the main fruity tobacco note.

EXAMPLE LXXXI

CHEWING TOBACCO

Onto 100 pounds of tobacco for chewing (85 percent Wisconsin leaf and 15 percent Pennsylvania leaf) the following casing is sprayed at a rate of 30 percent:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example XII | 0.4 |

The resultant product is redried to a moisture content of 20 percent. On chewing, this tobacco has an excellent substantially consistent, long-lasting cherry (20 minutes) nuance in conjunction with the main fruity tobacco note.

EXAMPLE LXXXII

CHEWING TOBACCO

Onto 100 pounds of tobacco for chewing (85 percent Wisconsin leaf and 15 percent Pennsylvania leaf) the following casing is sprayed at a rate of 30 percent:

| Ingredients | Parts by Weight |
| --- | --- |
| Corn Syrup | 60 |
| Licorice | 10 |
| Glycerine | 20 |
| Fig Juice | 4.6 |
| Prune Juice | 5 |
| Flavor Material of Example XIII | 0.4 |

The resultant product is redried to a moisture content of 20 percent. On chewing, this tobacco has an excellent substantially consistent, long-lasting cherry (20 minutes) nuance in conjunction with the main fruity tobacco note.

EXAMPLE LXXXIII

CHEWING TOBACCO

Onto 100 pounds of tobacco for chewing (85 percent Wisconsin leaf and 15 percent Pennsylvania leaf) the following casing is sprayed at a rate of 30 percent:

| Ingredients | Parts by Weight |
| --- | --- |
| Corn Syrup | 60 |
| Licorice | 10 |
| Glycerine | 20 |
| Fig Juice | 4.6 |
| Prune Juice | 5 |
| Flavor Material of Example XIX | 0.4 |

The resultant product is redried to a moisture content of 20 percent. On chewing, this tobacco has an excellent substantially consistent, long-lasting cherry (20 minutes) nuance in conjunction with the main fruity tobacco note.

EXAMPLE LXXXIV

The following mixture is prepared:

| Ingredient | Parts by Weight |
| --- | --- |
| Orange oil | 48.4 |
| Cab-O-Sil ® M-5 (Brand of Silica produced by the Cabot Corporation of 125 High Street, Boston, Mass. 02110; Physical Properties: Surface Area: 200 m²/gm Nominal Particle Size: 0.012 microns Density: 2.3 lbs./cu.ft.) | 3.2 |
| Xanthan gum | 4.2 |
| KLUCEL ® HF (Brand of hydroxypropyl cellulose produced by the Hercules Corporation of Wilmington, Delaware having a molecular weight of 800,000 and a viscosity defined according to FIG. 2) | 1.0 |

The Cab-O-Sil ®, hydroxypropyl cellulose and xanthan gum are intimately admixed. The resulting mixture of Cab-O-Sil, xanthan gum and hydroxypropyl cellulose is dispersed in the orange oil with vigorous stirring, thereby resulting in a viscous liquid. 48.4 Parts by weight of the powder flavor composition of Example Q is then blended into the said viscous liquid, with stirring at 25° C. for a period of 30 minutes resulting in a thixotropic sustained release flavor paste.

EXAMPLE LXXXV

The following mixture is prepared:

| Ingredient | Parts by Weight |
| --- | --- |
| Liquid flavor composition of Example A | 20 |
| Propylene glycol | 2 |
| Xanthan gum | 8.0 |
| KLUCEL ® EF (Brand of hydroxypropyl cellulose produced by the Hercules Corporation of Wilmington, Delaware having a molecular weight of 50,000 and a viscosity defined according to FIG. 2) | 2.0 |

The xanthan gum and hydroxypropyl cellulose are intimatley admixed. The resulting mixture of xanthan gum and hydroxypropyl cellulose is dispersed in the liquid flavor composition of Example A with vigorous stirring, thereby resulting in a viscous liquid. 70 Parts by weight of the powder flavor composition of Example R is then blended into the said viscous liquid, with stirring at 25° C. for a period of 30 minutes resulting in a dry, free flowing sustained release flavor powder.

EXAMPLE LXXXVI

The following mixture is prepared:

| Ingredient | Parts by Weight |
| --- | --- |
| Liquid flavor composition of Example A | 20 |
| Propylene glycol | 1 |
| Xanthan gum | 3 |
| Ethyl cellulose | 3 |
| KLUCEL ® LF (brand of hydroxypropyl) cellulose produced by Hercules Corporation of Wilmington, Delaware having a molecular weight of 100,000 and a viscosity defined according to FIG. 2) | 1.0 |

The xanthan gum, ethyl cellulose and hydroxypropyl cellulose are intimately admixed. The resulting mixture of xanthan gum, ethyl cellulose and hydroxypropyl cellulose is then dispersed in the liquid flavor composition of Example A with vigorous stirring, thereby resulting in a viscous liquid. 65 Parts by weight of the powder flavor composition of Example R is then blended into the said viscous liquid, with stirring at 25° C. for a period of 30 minutes resulting in a dry, free flowing sustained release flavor powder.

EXAMPLE LXXXVII

CHEWING GUM

100 Parts by weight of chicle are mixed with 4 parts by weight of the flavor prepared in accordance with Example LXXXIV. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into length of 3 inches each. On chewing, the chewing gum has a pleasant long lasting orange flavor.

EXAMPLE LXXXVIII

CHEWING GUM

100 Parts by weight of chicle are mixed with 18 parts by weight of the flavor prepared in accordance with Example LXXXIV. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into length of 3 inches each. On chewing, the chewing gum has a pleasant long lasting orange flavor.

EXAMPLE LXXXIX

CHEWING GUM

100 Parts by weight of chicle are mixed with 4 parts by weight of the flavor prepared in accordance with Example LXXXV. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into length of 3 inches each. On chewing, the chewing gum has a pleasant long lasting cherry flavor.

EXAMPLE XC

CHEWING GUM

100 Parts by weight of chicle are mixed with 18 parts by weight of the flavor prepared in accordance with Example LXXXV. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into length of 3 inches each. On chewing, the chewing gum has a pleasant long lasting cherry flavor.

EXAMPLE XCI

CHEWING GUM

100 Parts by weight of chicle are mixed with 4 parts by weight of the flavor prepared in accordance with Example LXXXVI. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into length of 3 inches each. On chewing, the chewing gum has a pleasant long lasting cherry flavor.

EXAMPLE XCII

CHEWING GUM

100 Parts by weight of chicle are mixed with 18 parts by weight of the flavor prepared in accordance with Example LXXXVI. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into length of 3 inches each. On chewing, the chewing gum has a pleasant long lasting cherry flavor.

What is claimed is:

1. A chewing gum comprising particles of a composition consisting essentially of:
   a. From about 3 up to about 7 parts by weight of a non-confined hydrophobic flavor oil;
   b. From about 3 up to about 7 parts by weight of a hydrolytically releaseable flavor oil physically entrapped in an edible solid material selected from the group consisting of gelatin, dextrin, gum acacia and modified food starch, said solid material having a particle size of from about 5 microns up to about 400 microns, said physically entrapped flavor oil being organoleptically compatible with said non-confined hydrophobic flvor oil;
   c. From about 0.1 up to about 1 part by weight of a solid suspending agent which is hydroxypropyl cellulose having a molecular weight of from about 50,000 up to about 800,000 and an all-enveloping mass of a chewable gum base within which said particles are substantially uniformly distributed whereby, as the chewing gum is chewed, the flavor is released at high flavor intensity substantially evenly and uniformly over an extended chewing time.

2. The chewing gum of claim 1 wherein the non-confined hydrophobic flavor oil is selected from the group consisting of cherry flavor oil, lemon flavor oil, lime flavor oil, orange oil, peppermint oil and oil of wintergreen.

3. The chewing gum of claim 1 wherein the flavor oil physically entrapped in the edible solid material is selected from the group consisting of:
   a. Cherry oil physically entrapped in modified food starch;
   b. Cherry oil encapsulated in gelatin capsules;
   c. Cherry flavor oil entrapped in gum acacia;
   d. Lemon oil physically entrapped in modified food starch;
   e. Lemon oil encapsulated in gelatin capsules;
   f. Lemon flavor oil entrapped in gum acacia;
   g. Lime oil physically entrapped in modified food starch;
   h. Lime oil encapsulated in gelatin capsules;
   i. Lime flavor oil entrapped in gum acacia;
   j. Peppermint oil physically entrapped in modified food starch;
   k. Peppermint oil encapsulated in gelatin capsules;
   l. Peppermint flavor oil entrapped in gum acacia;
   m. Oil of wintergreen physically entrapped in modified food starch;
   n. Oil of wintergreen encapsulated in gelatin capsules;
   o. Flavor oil of wintergreen entrapped in gum acacia;
   p. Orange oil physically entrapped in modified food starch;
   q. Orange oil encapsulated in gelatin capsules;
   r. Orange flavor oil entrapped in gum acacia;
   s. Cherry flavor oil entrapped in dextrin;
   t. Lemon oil encapsulated in dextrin;
   u. Lime flavor oil entrapped in dextrin;
   v. Peppermint flavor oil entrapped in dextrin;
   w. Oil of wintergreen entrapped in dextrin; and
   x. Orange flavor oil entrapped in dextrin.

4. The chewing gum of claim 1 wherein the composition has additionally added thereto from 0.03 up to 0.07 parts by weight of propylene glycol.

5. The method of preparing a chewing gum comprising:
(i) Admixing
   a. From about 3 up to 7 parts by weight of a non-confined hydrophobic flavor oil; and
   b. From about 0.1 up to about 1 part by weight of hydroxypropyl cellulose having the molecular weight of from about 50,000 up to about 800,000, thereby forming a first suspension;
(ii) Admixing said first suspension with from about 3 up to about 7 parts by weight of hydrolytically releaseable flavor oil physically entrapped in an edible solid material, selected from the group consisting of gelatin, dextrin, gum acacia and modified food starch, said solid material having a particle size of from about 5 microns up to about 400 microns thereby forming a second suspension, said physically entrapped flavor oil being organoleptically compatible with said non-confined hydrophobic flavor oil; and
(iii) Substantially uniformly distributing said second suspension within an all-enveloping mass of a chewable gum base.

6. The method of preparing chewing gum comprising the steps of:
   i. Forming an aqueous solution of a solid flavor entrapment material; selected from the group consisting of gelatin, dextrin, gum acacia and modified food starch;
   ii. Mixing therewith a first portion of a volatile, water immiscible flavoring agent thereby forming an emulsion;
   iii. Drying said emulsion thereby forming a solid flavoring agent;
   iv. Admixing a suspension agent therewith which is hydroxypropyl cellulose having a molecular weight of from about 50,000 up to about 800,000 with a second portion of said flavor agent to form a first suspension;
   v. Admixing said solid flavoring agent with said first suspension thereby forming a second suspension; and
   vi. Substantially uniformly distributing said second suspension within an all-enveloping mass of chewing gum base.

* * * * *